US010960083B2

(12) United States Patent
Grawunder et al.

(10) Patent No.: US 10,960,083 B2
(45) Date of Patent: Mar. 30, 2021

(54) BINDING PROTEIN DRUG CONJUGATES COMPRISING ANTHRACYCLINE DERIVATIVES

(71) Applicant: NBE-Therapeutics AG, Basel (CH)

(72) Inventors: Ulf Grawunder, Basel (CH); Roger Renzo Beerli, Basel (CH)

(73) Assignee: NBE-THERAPEUTICS AG, Basel (CH)

( * ) Notice: Subject to any disclaimer, the term of this patent is extended or adjusted under 35 U.S.C. 154(b) by 0 days.

(21) Appl. No.: 16/555,725

(22) Filed: Aug. 29, 2019

(65) Prior Publication Data

US 2020/0093933 A1   Mar. 26, 2020

Related U.S. Application Data

(60) Division of application No. 16/138,347, filed on Sep. 21, 2018, now Pat. No. 10,517,959, which is a continuation of application No. 15/539,518, filed as application No. PCT/EP2015/081183 on Dec. 23, 2015, now Pat. No. 10,188,745.

(60) Provisional application No. 62/095,820, filed on Dec. 23, 2014.

(51) Int. Cl.
  *A61K 47/68* (2017.01)
  *A61K 47/64* (2017.01)
  *C12P 21/02* (2006.01)

(52) U.S. Cl.
  CPC .......... *A61K 47/6803* (2017.08); *A61K 47/64* (2017.08); *A61K 47/6809* (2017.08); *A61K 47/6849* (2017.08); *A61K 47/6855* (2017.08); *A61K 47/6867* (2017.08); *A61K 47/6871* (2017.08); *A61K 47/6889* (2017.08); *C12P 21/02* (2013.01); *C12Y 304/2207* (2013.01)

(58) Field of Classification Search
  CPC ............... A61K 47/6803; A61K 47/64; A61K 47/6809; A61K 47/6855; A61K 47/6867; A61K 47/6889; A61K 47/6871; A61K 47/6849; C12P 21/02; C12Y 304/2207
  See application file for complete search history.

(56) References Cited

U.S. PATENT DOCUMENTS

| | | | |
|---|---|---|---|
| 8,389,697 B2 | 3/2013 | Beria et al. | |
| 8,470,984 B2 | 6/2013 | Caruso et al. | |
| 8,742,076 B2 | 6/2014 | Cohen et al. | |
| 8,900,589 B2 | 12/2014 | Beria et al. | |
| 9,492,553 B2 | 11/2016 | Cohen et al. | |
| 9,695,240 B2 | 7/2017 | Beria et al. | |
| 9,872,923 B2 | 1/2018 | Grawunder et al. | |
| 2004/0077842 A1 | 4/2004 | Himawan | |
| 2010/0055761 A1 | 3/2010 | Seed et al. | |
| 2010/0111851 A1 | 5/2010 | Aburatani et al. | |
| 2011/0321183 A1 | 12/2011 | Ploegh et al. | |

FOREIGN PATENT DOCUMENTS

| | | |
|---|---|---|
| JP | 2008-523062 A | 7/2008 |
| JP | 2012-519711 A | 8/2012 |
| JP | 2012-523383 A | 10/2012 |
| WO | WO 2006/062779 A2 | 6/2006 |
| WO | WO 2007/076974 A2 | 7/2007 |
| WO | WO 2007/108013 A2 | 9/2007 |
| WO | WO 2009/099741 A1 | 8/2009 |
| WO | WO 2009/132455 A1 | 11/2009 |
| WO | WO 2010/009124 A1 | 1/2010 |
| WO | WO 2010/111018 A1 | 9/2010 |
| WO | WO 2010/115630 A1 | 10/2010 |
| WO | WO 2011/133704 A1 | 10/2011 |
| WO | WO 2012/073217 A1 | 6/2012 |
| WO | WO 2012/142659 A2 | 10/2012 |
| WO | WO 2013/022808 A2 | 2/2013 |
| WO | WO 2013/177055 A1 | 11/2013 |
| WO | WO 2014/088928 A1 | 6/2014 |
| WO | WO 2014/140317 A2 | 9/2014 |

OTHER PUBLICATIONS

Alley et al. (2008) "Contribution of linker stability to the activities of anticancer immunoconjugates," Bioconjug Chem. Epub, 19(3):759-65.
Ardelt et al. (2008) "Onconase and amphinase, the antitumor ribonucleases from Rana pipiens oocytes," Curr Pharm Biotechnol., 9(3): 215-25.
Baer et al. (2014) "Comparison of alternative nucleophiles for Sortase A-mediated bioconjugation and application in neuronal cell labelling," Org Biomol Chem.; 12(17): 2675-85.
Beerli et al. (2015) "Sortase Enzyme-Mediated Generation of Site-Specifically Conjugated Antibody Drug Conjugates with High In Vitro Potency," PLoS ONE 10(7):e0131177, 17 pages.
Crooke et al. (1981) "The anthracyclines, Cancer and Chemotherapy, vol. III, Antineoplastic Agents," Academic Press, Inc, Chapter 8, pp. 111-132.
Dokter et al. (2014) "Preclinical profile of the HER2-targeting ADC SYD983/SYD985: introduction of a new duocarmycin-based linker-drug platform," Mol. Cancer. Ther., 13(11):2618-29.
Dorr et al. (2014) "Reprogramming the specificity of sortase enzymes," PNAS, 111(37):13343-13348.
Ducry et al. (2010) "Antibody-drug conjugates: linking cytotoxic payloads to monoclonal antibodies," Bioconjug. Chem., 21(1):5-13.
Hartley et al. (2012) "Small molecule drugs—optimizing DNA damaging agent-based therapeutics," Curr. Opin. Pharmacol., 12(4):398-402.
International Search Report and Written Opinion for Application No. PCT/EP2014/055173, dated Oct. 24, 2014, 21 pages.

(Continued)

*Primary Examiner* — Shirley V Gembeh
(74) *Attorney, Agent, or Firm* — Morgan, Lewis & Bockius LLP; Christopher J. Betti; Alia M. Orbin

(57) ABSTRACT

The present invention relates to an anthracycline (PNU) derivative conjugate comprising a derivative of the anthracycline PNU-159682 having the formula (i) or formula (ii) which further comprises a linker structure X-L1-L2-L3-Y.

13 Claims, 13 Drawing Sheets

Figure 1:
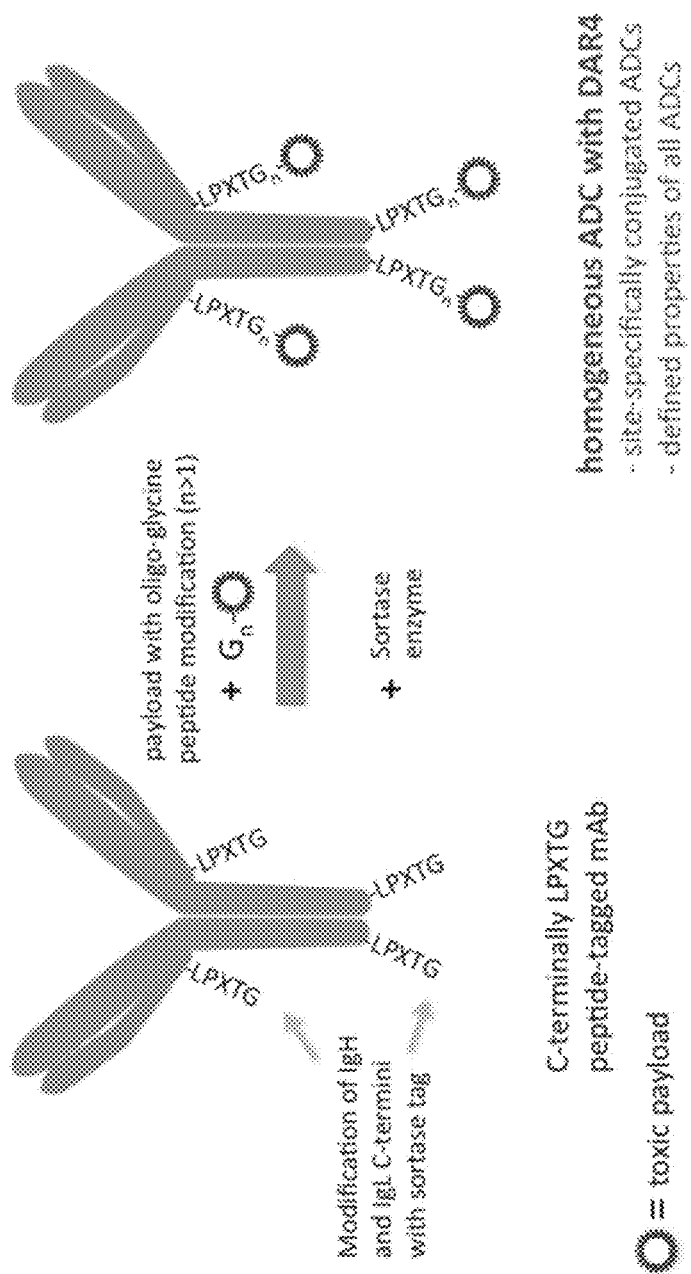

Specification includes a Sequence Listing.

(56) References Cited

OTHER PUBLICATIONS

International Search Report and Written Opinion for Application No. PCT/EP2015/081183, dated Oct. 16, 2016, 12 pages.
Jain et al. (2015) Current ADC Linker Chemistry, Pharm Res. Nov; 32{11}:3526-40. doi: 10.1007/11095-015-1657-7. Epub.
LoRusso, P.M., et al. (2011) "Trastuzumab emtansine: a unique antibody-drug conjugate in development for human pidermal growth factor receptor 2-positive cancer," Clin Cancer Res, v. 17, pp. 6437-6447.
Madej et al. (2012) "Engineering of an anti-epidermal growth factor receptor antibody to single chain format and labeling by Sortase A-mediated protein ligation," Biotechnol Bioeng., 109(6): 1461-70.
McCluskey et al. (2013) "Receptor-directed chimeric toxins created by sortase-mediated protein fusion," Mol Cancer Ther.; 12(10): 2273-81.
McCombs et al. (2015) "Antibody Drugh Conjugates: Design and Selection of Linker, Payload and Conjugation Chemistry," AAPS J., 17(2):339-351.
Minotti et al. (2004) "Anthracyclines: molecular advances and pharmacologic developments in antitumor activity and cardiotoxicity," Pharmacol. Rev, 56(2):185-229.
Mullard et al. (2013) "Maturing antibody-drug conjugates pipeline hits 30," Nature Rev. Drug Disc., vol. 12, 329-332.
Panowski et al. (2014) "Site-specific antibody drug conjugates for cancer therapy," mAbs, 6(1):34-45.
Perez et al. (2014) "Antibody-drug conjugates: current status and future directions," Drug Discov. Today, 19(7):869-81.
Quintieri et al. (2005) "Formation and antitumor activity of PNU-159682, a major metabolite of nemorubicin in human liver microsomes", Clinical Cancer Research vol. 11, Issue 4, Feb. 2005.
Roguska et al. (1994) "Humanization of murine monoclonal antibodies through variable domain resurfacing," PNAS, 91(3):969-973.
Song et al. (2012) "Protein Trans-Splicing of an Atypical Split Intein Showing Structural Flexibility and Cross-Reactivity," PLoS One.; 7(9): e45355.
Spirig et al. (2011) "Sortase enzymes in Gram-positive bacteria," Mol. Microbiol., 82:1044-1059.
Swee et al. (2013) "Sortase-mediated modification of alpha DEC205 affords optimization of antigen presentation and immunization against a set of viral epitopes," Proc Natl Acad Sci USA, 110:4.
Ta et al. (2011) "Enzymatic single-chain antibody tagging: a universal approach to targeted molecular imaging and cell homing in cardiovascular disease," Circ. Res.; 109(4): 365-73.
Ta, H. T. et al. (2012) "Enzymatic Antibody Tagging: Toward a Universal Biocompatible Targeting Tool," Trends in Cardiovascular Medicine, v. 22, pp. 105-111.
Tsukiji et al. (2009) "Sortase-Mediated Ligation: A Gift from Gram-Positive Bacteria to Protein Engineering," Chembiochem—A European Journal of Chemical Biology, vol. 10, No. 5, pp. 787-798.
Volkmann et al. (2009) "Protein C-terminallabeling and biotinylation using synthetic peptide and split-intein," PLoS One.; 4(12): e8381.
Wolff et al. (2013) "Recommendations for Human Epidermal Growth Factor Receptor 2 Testing in Breast Cancer: American Society of Clinical Oncology/College of American Pathologists Clinical Practice Guideline Update," J. Clin. Oncol., 31:3997-4013.
Younes et al. (2010) New England Journal of Medicine, vol. 363, pp. 1812-1821.
Young et al. (2014) "CD30 Diagnostics and Testing," Clin. Adv. Hematol. Oncol., 12(4): Supplement 10, pp. 9-15.

formula (vii)

formula (viii)

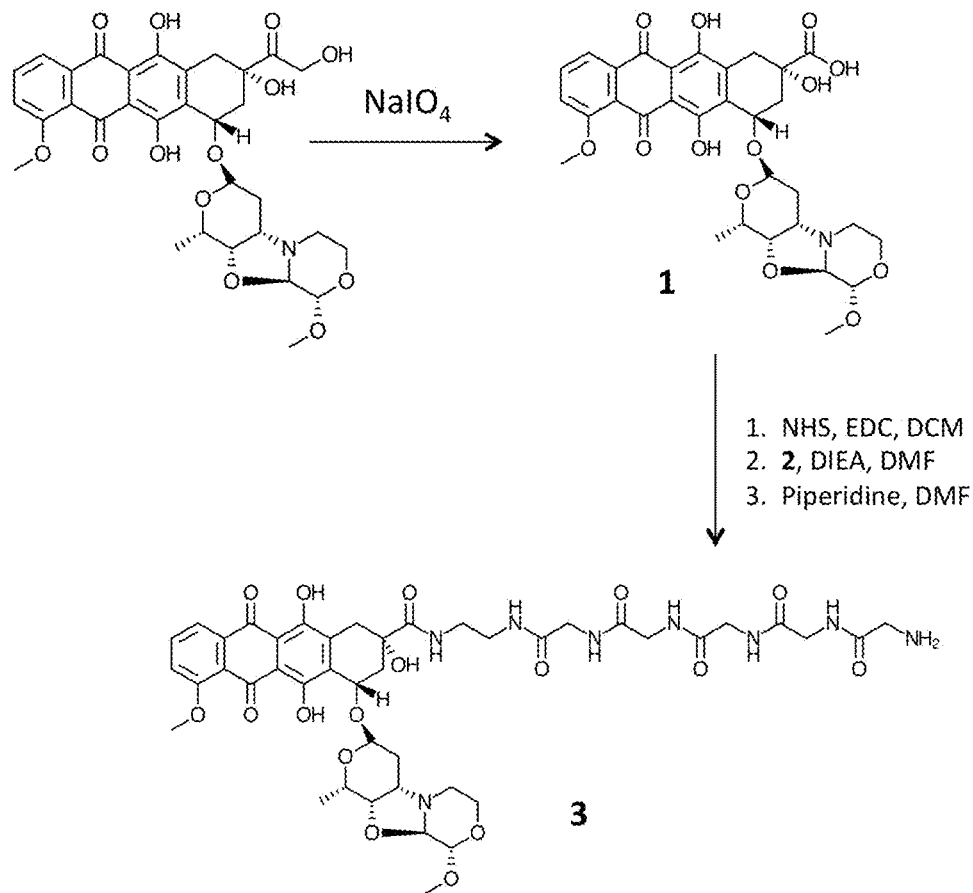
Where 2 corresponds to:
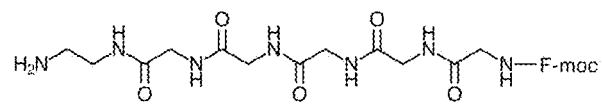
Fig. 3B

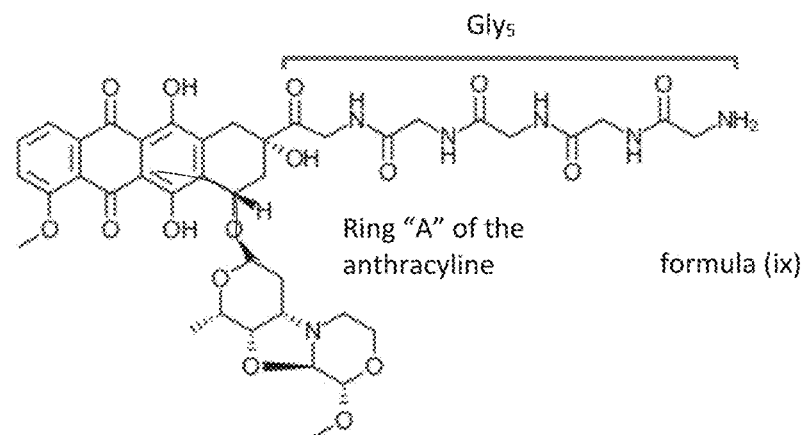
Fig. 6A: PNU-Gly₅
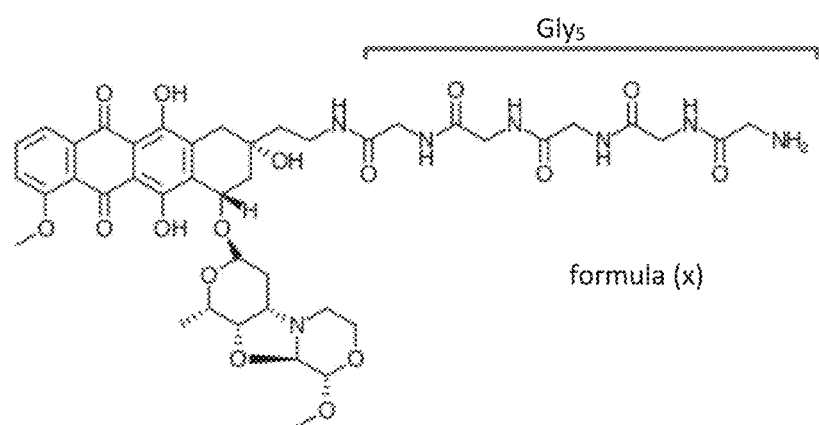
Fig. 6B: PNU-EA-Gly₅

Fig. 11 A:

*Trastuzumab-HC-LPETGGGGG-PNU-toxin*

EVQLV

Fig. 11 B

*Brentuximab-HC-LPETGGGGG-PNU-toxin*

QIQLQQSGPE

BINDING PROTEIN DRUG CONJUGATES COMPRISING ANTHRACYCLINE DERIVATIVES

CROSS-REFERENCE TO RELATED APPLICATIONS

This application is a division of U.S. patent application Ser. No. 16/138,347, filed Sep. 21, 2018, which is a continuation of U.S. patent application Ser. No. 15/539,518, filed Jun. 23, 2017, now U.S. Pat. No. 10,188,745, which is a 35 U.S.C. § 371 filing of International Patent Application No. PCT/EP2015/081183, filed Dec. 23, 2015, which claims the benefit of priority to U.S. Provisional Patent Application Ser. No. 62/095,820, filed Dec. 23, 2014. The entire contents of these applications are incorporated herein by reference for all purposes.

The present invention relates to binding protein drug conjugates comprising anthracycline toxin derivatives

INTRODUCTION

Covalent conjugates of small molecular weight toxins (MW preferably <2'500 daltons) to binding proteins, in particular to antibodies specific for tumor cells, are powerful tools to specifically target cancer cells for their destruction. Therefore, such binding protein drug conjugates (BPDCs), particularly antibody drug conjugates (ADCs), are of high medical and commercial interest for the therapy of cancer. In order to develop effective and safe BPDCs or ADCs for cancer therapy, several aspects need to be addressed: First, the binding protein or antibody needs to be specific for a given tumor specific antigen (TSA), which should hardly or ideally not be expressed by normal or healthy tissue cells. Second, the covalent bond, or linkage, between the drug and the binding protein needs to have the functionality to be stable enough in circulation, preventing undesired release of the toxic payload in the blood stream, but it has to effectively release the drug upon binding to and/or internalization into the cancer cells. Third, the toxic payload has to be of high enough toxicity, or potency, in order to effect the destruction of the cancer cells, even if potentially limited amounts of the TSA are expressed on the cancer cells and therefore only limited amounts of the ADC are internalized, or if release of the toxic payload is not effected at high enough efficiency upon binding to the cancer cells, or upon internalization into the cancer cell.

While the first aspect of successfully targeting cancer via a TSA depends on a deep understanding of the target biology and the targeting molecules developed for its specific binding, the second and third aspects, related to optimal linker and to toxin payload, generally applies to the effectiveness of binding protein drug conjugates (BPDCs) or antibody drug conjugates (ADCs).

All ADCs currently in clinical trials, and the two ADCs that are FDA-approved for cancer treatment, anti-CD30 ADC Adcetris® (brentuxumab-vedotin) from Takeda, and anti-HER-2 ADC Kadcyla® (trastuzumab emtansine, or T-DM1) from Roche/Genentech (see Perez et al. 2014), are generated by chemical conjugation of toxic payloads involving maleimide linker chemistry either to primary amino groups of lysine residues of the antibody, or to free thiol groups, generated by mild reduction of antibody intra-chain disulfide bridges. The chemical conjugation has two limitations: First, it has been found that chemical maleimide-based linkers are associated with an undesired instability in the presence of human serum albumin and thus lead to release of toxins in circulation of patients treated with maleimide-linker containing ADCs (see Alley et al., 2008). Second, classical chemical conjugation by maleimide linker chemistry results in heterogeneous BPDCs or ADCs, because it cannot be controlled to which amino- or thiol groups the conjugation occurs. Therefore, a Gaussian distribution of number of drugs covalently bound per antibody is obtained, such that conjugated ADCs have an average drug-to-antibody ratio (DAR) ranging between 3.5 and 4. However, individual conjugates may have no drug attached (DAR=0) to the antibody, or up to 8 drugs attached to the antibody (DAR=8) in case of cysteine conjugates and even more drugs per antibody (>DAR 10) in case of lysine conjugates. Classical chemically conjugated ADCs therefore represent a heterogeneous mixture of different molecules exhibiting different functional properties (see Panowski et al., 2014), which clearly is undesirable from a regulatory point of view in developing ADCs for treatment of cancer patients.

Therefore, there is a commercial and medical need to provide ADCs or BPDCs that are site-specifically conjugated, and thus are homogeneous with regard to the drug-to-antibody ratio.

In addition, there is a commercial and medical need to provide ADCs or BPDCs with more stable drug to protein linkage that are more stable in blood circulation than the traditional conjugates based on maleimide linker chemistry.

Further, there is a commercial and medical need to provide ADCs or BPDCs that have a higher efficacy and less side effects than ADCs or BPDCs currently on the market.

GENERAL FEATURES OF THE INVENTION

The present invention solves these problems. It provides now toxins for use in binding protein-drug conjugates, plus optionally a new technology to conjugate these toxins to the said binding proteins in a site-specific manner by avoiding classical maleimide linker chemistry.

The general advantages of these two features will be discussed in the following:

Linker Technology

Both, the above-mentioned serum instability and the heterogeneity of chemically conjugated, and maleimide-linker containing BPDCs or ADCs represent significant liabilities for the safety of these drugs in cancer patients, because both add to the non-specific release of the toxin ("de-drugging") of such ADCs in patients.

On one hand, the classical maleimide linkers can be broken up by free thiols in human serum, in particular cysteine-34 of human serum albumin, which—as the most abundant serum protein—provides the highest concentration of free thiols in human serum. Cysteine-34 of human serum albumin can break the thioether bond of maleimide linkers by way of a so-called retro-Michael reaction upon which the toxin is transferred and covalently coupled to human serum albumin (HSA). The toxin-HSA conjugate can then distribute the toxin in circulation or in the body without any tumor selectivity (see: Alley et al., 2008).

On the other hand, the higher DAR-species in the chemically conjugated, heterogeneous ADCs are known to have shorter serum half-lives due to a higher hydrophobicity of these ADCs and a propensity for aggregation. Therefore these higher DAR species are subject to faster clearance from serum, degradation and release of the toxin prior to the binding of these ADC to target positive cancer cells. In addition, higher DAR species are also known to lead to a faster de-drugging, because individual conjugation sites have different de-drugging kinetics, depending on the structural context of the amino acid carrying the toxin.

The above-mentioned liabilities of chemically conjugated ADCs have impeded success of developing ADCs into the clinic, despite the fact that the concept of delivering a highly potent cellular toxin to cancer cells via its coupling to a tumor cell-specific antibody is compelling. Due to toxin-related side-effects the first ADC that had been FDA-approved in 2000, Mylotarg® (gemtuzumab ozogamicin) from Pfizer/Wyeth, needed to be taken off the market 10 years after FDA-approval (http://www.fda.gov/NewsEvents/Newsroom/PressAnnouncements/ucm2164 48.htm).

The liabilities of chemically conjugated ADCs therefore restricts current ADC development efforts to toxins with intermediate cellular toxicity, like e.g. tubulin polymerization inhibiting dolastatin/auristatin-based and maytansin-based drugs. In fact, more than 90% of all ADCs currently in clinical evaluation carry toxins related to monomethyl auristatin E (MMAE) or F (MMAF) or to maytansine (e.g. DM1 or DM4) (see: Mullard (2013))

However, tubulin polymerization inhibiting drugs cannot reach potencies below the nanomolar range, because tubulin, a component of the cellular cytoskeleton, is a highly abundant intracellular protein target, so that many drug molecules need to diffuse or be transported into the cell, in order to shut down metabolism of the intracellular cytoskeleton, required for cell division and survival. The intermediate potency of tubulin polymerization inhibiting drugs, which can tolerate a certain degree of "de-drugging" of conjugates, and their specific action on dividing and mitotic cells has made toxins with this particular mode of action most popular for the development of ADCs.

However, in order to specifically address tumors with low expression level of TSAs, much higher potent toxins will be required. Therefore, newer ADC strategies, still in preclinical development involve toxins with high cellular toxicity and different mode of actions, in particular DNA damaging toxins, like duocarmycins (see: Doktor et al. (2014) and pyrrolobenzodiazepines (PBDs) (see: Hartley & Hochhauser (2012)).

Anthracycline Derivatives

A highly interesting class of DNA intercalating toxins for use as payloads for BPDCs or ADCs are anthracyclines, because of their proven clinical validation as chemotherapeutic drugs in cancer therapy (see: Minotti (2004)) Anthracyclines are red-colored polyketides with high anti-tumor activity, originally derived from *streptomyces* species. Many derivatives have been described during the last 40 years, including some that are routinely used as chemotherapy drug for various solid and hematological cancers, e.g. doxorubicin (also called adriamycin), daunorubicin, epirubicin, idarubicin, or valrubicine. There is even one anti-CD74 ADC in phase I/II clinical trials for multiple myeloma and other hematological cancers with doxorubicin as a toxic payload, milatuzmab-doxorubicin (see: clinicaltrials.gov identifier: NCT01101594).

All of the anthracycline-based chemotherapeutic drugs are known to show limited potency on tumor cells as free drugs with $IC_{50S}$ in the µmol/ml range on most tumor cells (Crooke and Prestayko, 1981). Despite the example of a first doxorubin-ADC currently evaluated in clinical trials, the use of conventional anthracyclines as toxic payloads for ADC strategies is likely to remain challenging.

About a decade ago, a novel anthracycline derivative, called PNU-159682, has been described as a metabolite of nemorubicin (see: Quintieri et al. (2005) Clin. Cancer Res. 11, 1608-1617), which has recently been reported to exhibit extremely high potency for in vitro cell killing in the pico- to femtomolar range with one ovarian (A2780) and one breast cancer (MCF7) cell line (WO2012/073217 A1, Caruso et al.). The structure of the anthracycline derivative PNU-159682, as disclosed in the above-mentioned prior art documents is disclosed in FIG. 2 for the purpose of reference, and with the official anthracycline numbering system for reactive carbons of the tetracyclic aglycone structure.

Based on the above-mentioned limitations of chemically conjugated ADCs, with regard to maleimide-linker instability and de-drugging of higher DAR species in heterogeneous chemically conjugated ADCs, a highly potent anthracycline toxin, like PNU-159682, is expected to be highly problematic in the context of classical chemical conjugation, due to release of the toxin in circulation prior to targeting of the tumor cells.

Therefore potent toxins, as e.g. PNU-159682, homogeneous ADCs with defined pharmacokinetic properties and extended serum stability are required, in order to avoid, or to minimize side effects from prematurely released toxins in circulation of patients. However, at the same time, specific killing of tumor cells characterized by low target expression still needs to be possible.

Although the use of PNU-159682 as a payload for ADC generated by classical chemical maleimide linker approaches has been disclosed before (WO2009/099741 A1, Cohen et al.), no functional data were provided in this prior art document. First functional data with PNU-159682 linked to antibodies with different linker and spacer structures in the context of chemically conjugated and heterogenous maleimide-linker containing conjugates on tumor cells were disclosed in the prior art document WO2010/009124 A2 (Beria et al.), but safety and pharmacokinetic data was not provided.

PREFERRED EMBODIMENTS

According to a first preferred embodiment, anthracycline (PNU) derivative conjugates are described that contain PNU-159682 derivatives lacking the C14 carbon and attached hydroxyl group of the tetracyclic aglycone structure characteristic for anthracyclines. As a second preferred embodiment anthracycline (PNU) derivative conjugates are described lacking both the C13 and C14 carbons with carbonyl function at C13 and hydroxyl group at C14 of the teracyclic aglycone structure characteristic for anthracyclines.

In these embodiments, the anthracycline (PNU) derivative conjugates comprise a derivative of the anthracycline PNU-159682 having the following formula (i) or formula (ii):

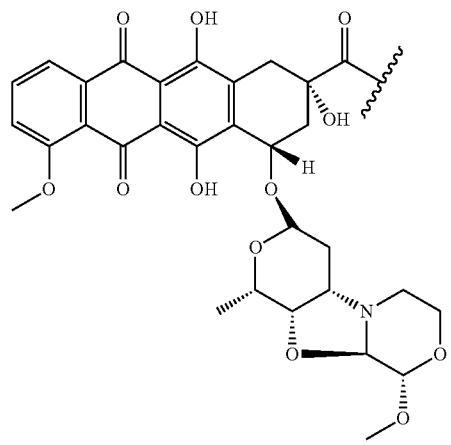

formula (i)

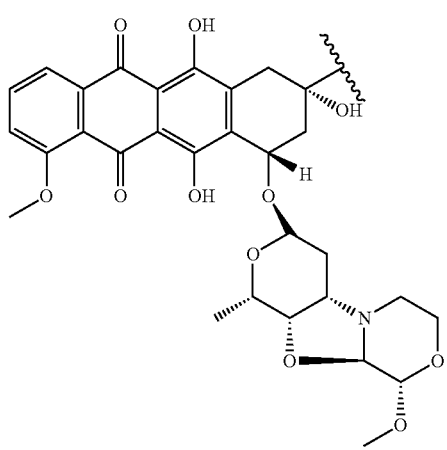

formula (ii)

Said conjugates comprise at their wavy line a linker structure that can have different elements, $X-L_1-L_2-L_3-Y$, wherein $L_1-L_3$ represent linkers, and two of $L_1-L_3$ are optional, and wherein X and Y further represent each one or more optional linkers.

Both derivatives are markedly different to PNU-159682, which is a metabolite of the anthracycline nemorubicin and has for the first time been disclosed by Quintieri et al. (2005).

Both C13 and C14 carbons with their carbonyl function at C13 and the hydroxyl group at C14 are a mandatory structural feature of PNU-159682, which are not part of the derivative conjugates disclosed herein.

Figure 3A:
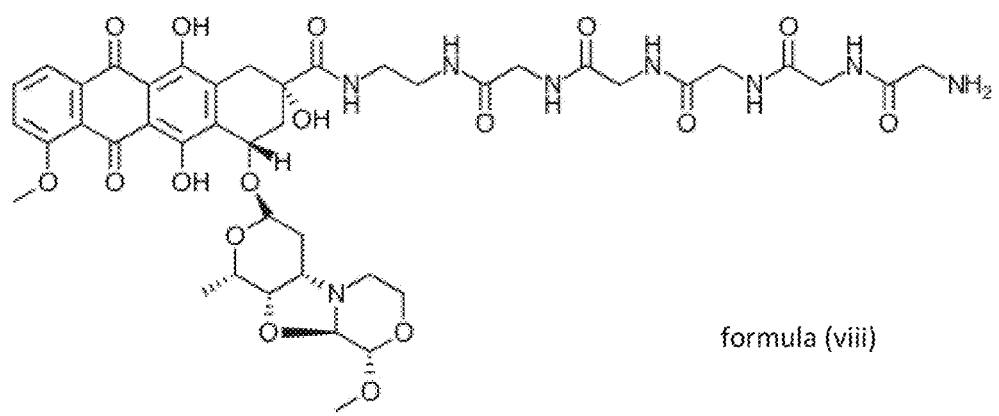

Surprisingly, and for the first time, it is demonstrated that PNU-derivatives without carbon 14 and attached hydroxyl group of the tetracyclic aglycone structure characteristic for anthracyclines exhibit cellular toxicity, e.g., in site-specifically conjugated antibody drug conjugates. Preferred embodiments thereof are shown in FIGS. 3A, 6A and 6B.

According to another embodiment of the invention, a binding protein-drug conjugate (BPDC) is provided, having the following formula:

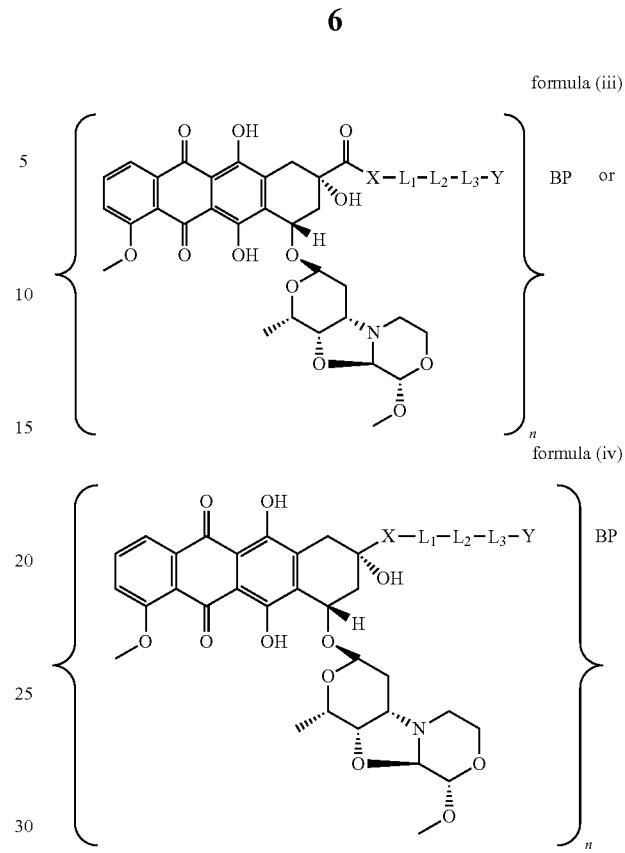

wherein $L_1-L_3$ represent linkers, and two of $L_1-L_3$ are mandatory, wherein X any Y represent each one or more optional linker, wherein BP is a binding protein, and wherein n is an integer between $\geq 1$ and $\leq 10$.

In this construct, several linkers can form a unitary chain that conjugates one toxin to the one binding protein, and/or several linkers can connect several toxins to the one binding protein. Likewise, the linkers can conjugate two or more subunits of the same binding protein to two or more toxin molecules.

The optional linker X can be any chemical linker structure known in the prior art, that have been used in ADCs to allow specific release of the toxin upon internalization into cancer cells (see e.g. Ducry & Stump (2010) or McCombs et al. (2015)

Some examples for such linkers described in the prior art, which are only provided by way of example and not intended to be limiting, are shown below.

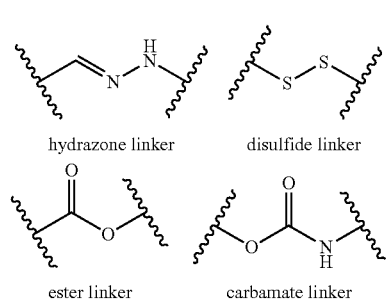

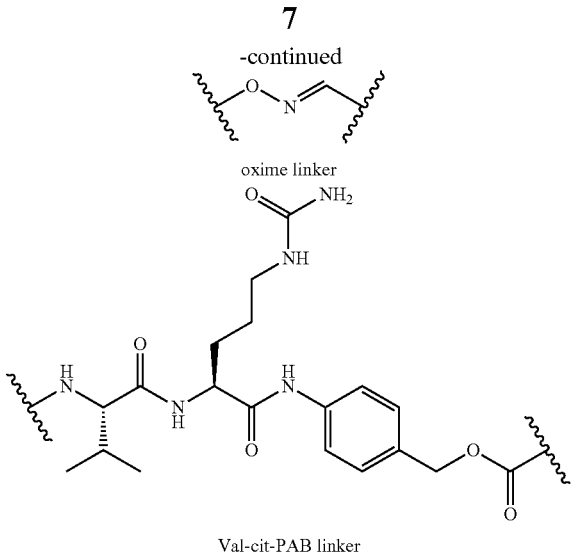

oxime linker

Val-cit-PAB linker

Linkers $L_1$, $L_2$ and $L_3$ are discussed below.

The optional linker Y can be any chain of amino acids with up to 20 amino acids allowing optimal conjugation of the binding protein to the unitary chain of linkers X, $L_1$, $L_2$, $L_3$ or variations thereof, in particular to $L_3$.

Furthermore, linker structures are provided, that allow site-specific conjugation of the PNU-derivatives to suitable binding proteins, e.g, and preferably to antibodies. The derivatives can thus be used to produce site-specifically conjugated, homogeneous binding protein-drug conjugates, which can be used in therapeutic applications, like anti cancer therapy.

According to another preferred embodiment of the anthracycline (PNU) derivative, the linker structure comprises, as $L_2$, an oligo-glycine peptide $(Gly)_n$ coupled to said anthracycline derivative, directly or by means of another linker $L_1$, in such a way that the oligo-glycine $(Gly)_n$ peptide has a free amino terminus, and wherein n is an integer between $\geq 1$ and $\leq 21$.

In each case $(Gly)_n$ (also called $(Gly)_n$-$NH_2$ or $Gly_n$-stretch herein) is a an oligo-glycine peptide-stretch. In one particularly preferred embodiment, n is an integer between $\geq 3$ and $\leq 10$, preferably $\geq 3$ and $\leq 6$. Most preferred, n=5.

As already disclosed herein, the anthracycline (PNU) derivatives disclosed herein are derivatives of PNU-159682 either lacking carbon atom 13 and 14 or lacking only carbon 14 with attached functional groups.

With respect to formula (i), it is one preferred embodiment that the oligo-glycine peptide $(Gly)_n$ ($\geq 1$ and $\leq 21$, preferably n=3 or n=5) is conjugated to the anthracycline derivative by means of an alkylenediamino linker ($NH_2$—$(CH_2)_m$—$NH_2$, m$\geq 1$ and $\leq 11$, preferably m=2), which is conjugated to the anthracycline derivative by means of a first amide bond to carbon 13 and conjugated to the carboxyterminus of the oligo-glycine peptide by means of a second amide bond. The preferred compound, PNU-EDA-Gly$_5$, useful for generating site-specifically conjugated anthracycline (PNU) derivative conjugates is depicted in FIG. 3A.

With respect to formula (ii), it is a preferred embodiment that the oligo-glycine peptide $(Gly)_n$ ($\geq 1$ and $\leq 21$, preferably n=3 or n=5) is directly coupled to Ring A of the PNU derivative (or carbon 9 of the anthracycline aglycone structure), such that the carbonyl group of carbon 13 represents the carboxy-end of the glycine peptide linker. The preferred compound, PNU-Gly$_5$, useful for generating site-specifically conjugated anthracycline (PNU) derivative conjugates is depicted in FIG. 6A.

With respect to formula (ii), it is another preferred embodiment that the oligo-glycine peptide $(Gly)_n$ ($\geq 1$ and $\leq 21$, preferably n=3 or n=5) is conjugated directly to Ring A of the PNU derivative (or carbon 9 of the anthracycline aglycone structure), with a alkyleneamine linker —$(CH_2)_m$—$NH_2$, m$\geq 1$ and $\leq 11$, preferably m=2) that is conjugated to the carboxyterminus of the oligo-glycine peptide by means of an amide bond. The preferred compound, PNU-EA-Gly$_5$ useful for generating site-specifically conjugated PNU-derivative conjugates is depicted in FIG. 6B.

In the following, the anthracycline derivative conjugates according to the above description are also called "PNU-EDA-Gly$_n$-NH$_2$", "PNU-Gly$_n$-NH$_2$" or "PNU-EA-Gly$_n$-NH$_2$", or in short also "PNU-EDA-Gly$_n$", "PNU-Gly$_n$", or "PNU-EA-Gly$_n$", respectively, or in its preferred embodiment with 5 glycine residues, "PNU-EDA-Gly5", "PNU-Gly5", or "PNU-EA-Gly5", respectively.

The invention further provides a binding protein-drug conjugate (BPDC), comprising an anthracycline derivative conjugate according to the above disclosure, which derivative further comprises a binding protein conjugated to the free amino terminus of the oligo-glycine peptide $(Gly)_n$ by means of an additional amide bond.

According to another embodiment of the anthracycline (PNU) derivative or the binding protein-drug conjugate (BPDC), the oligo-glycine peptide $(Gly)_n$, designated as L2, is conjugated to the anthracycline derivative of formula (i) by means of an alkylenediamino linker, designated as $L_1$, which alkylenediamino linker is conjugated to the anthracycline derivative by means of a first amide bond, while it is conjugated to the carboxy terminus of the oligo-glycine peptide by means of a second amide bond, said conjugate of alkylenediamino linker and oligo-glycine peptide having the following formula (v), formula (v)

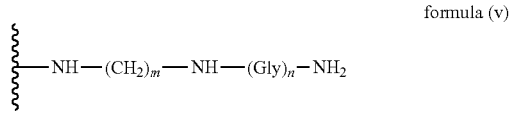

wherein the wavy line indicates the linkage to the anthracycline derivative of formula (i).

m is an integer between $\geq 1$ and $\leq 11$, and n is an integer between $\geq 1$ and $\leq 21$. Preferably, m is an integer between $\geq 2$ and $\leq 4$, most preferably m=2 (ethylenediamino group, EDA).

The alkylenediamino linker is used to allow attachment of the $(Gly)_n$ linker for sortase conjugation, such that the coupling can occur via the C-terminus of the $(Gly)_n$ peptide, thus providing a free N-terminus of the final toxin-linker adduct for sortase conjugation. It is to be understood that any $CH_2$ methylene group in the alkylenediamino linker may be substituted by another stable bond, e.g. an —O— (ether), —S— (thioether), —NH— (amine), or any other alkyl, hetero-alkyl, aryl or hetero-aryl group, or any combination thereof, in order to realize the invention.

According to another embodiment of the anthracycline (PNU) derivative or the binding protein-drug conjugate (BPDC), the oligo-glycine peptide $(Gly)_n$ is directly coupled to Ring A (or carbon 9) of the anthracycline derivative of formula (ii). See FIG. 6A for an illustration thereof.

According to another embodiment of the anthracycline (PNU) derivative or the binding protein-drug conjugate (BPDC), the oligo-glycine peptide $(Gly_n)$ is conjugated to the anthracycline derivative of formula (ii) by means of an alkyleneamino linker, designated as $L_1$, which alkyleneamino linker is conjugated to the carboxy terminus of the oligo-glycine peptide by means of an amide bond, said conjugate of alkyleneamino linker and oligo-glycine peptide having the following formula (vi)

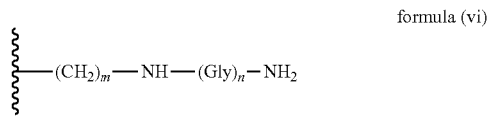

formula (vi)

wherein the wavy line indicates the linkage to the anthracycline derivative of formula (ii), wherein m is an integer between $\geq 1$ and $\leq 11$, and n is an integer between $\geq 1$ and $\leq 11$. Preferably, m is an integer between $\geq 2$ and $\leq 4$, most preferably m=2 (ethyleneamino group, EA).

The alkyleneamino linker is used to allow attachment of the $(Gly)_n$ linker for sortase conjugation, such that the coupling can occur via the C-terminus of the $(Gly)_n$ peptide, thus providing a free N-terminus of the final toxin-linker adduct for sortase conjugation. It is to be understood that any $CH_2$ methylene group in the alkyleneamino linker may be substituted by another stable bond, e.g. an —O— (ether), —S— (thioether), —NH— (amine), or any other alkyl, hetero-alkyl, aryl or hetero-aryl group, or any combination thereof, in order to realize the invention.

In another embodiment of the binding protein-drug conjugate (BPDC), the linker structure $L_3$ comprises a peptide motif that results from specific cleavage of a sortase enzyme recognition motif.

As disclosed elsewhere herein as well as in WO2014140317, content of which is incorporated by reference herein, sortases (also called sortase transpeptidases) form a group of prokaryotic enzymes that modify surface proteins by recognizing and cleaving a specific sorting signal comprising a particular peptide motif. This peptide motif is also called "sortase enzyme recognition motif", "sortase tag" or "sortase recognition tag" herein. Usually, a given sortase enzyme has one or more sortase enzyme recognition motifs that are recognized. Sortase enzymes can be naturally occurring, or may have undergone genetic engineering (Doerr et al., 2014).

In a preferred embodiment of the binding protein-drug conjugate (BPDC), said sortase enzyme recognition motif comprises a pentapeptide.

In preferred embodiment of the binding protein-drug conjugate (BPDC), said sortase enzyme recognition motif comprises at least one of the following amino acid sequences (shown N-terminus→C-terminus):
LPXTG
LPXSG, and/or
LAXTG.

The first two sortase enzyme recognition motifs are recognized by wild type *Staphylococcus aureus* sortase A. The second one is also recognized by engineered sortase A 4S9 from *Staphylococcus aureus*, and the third one is recognized by engineered sortase A 2A-9 from *Staphylococcus aureus* (Doerr et al, 2014). In all three cases, X can be any of the 20 peptidogenic amino acids.

These sortase enzyme recognition motifs are, for example, fused to the C-terminus of a binding protein, or a domain or subunit thereof, by genetic fusion, and are co-expressed therewith. Said fusion can be done directly, or indirectly, via additional linker Y described elsewhere herein, It is noteworthy that, once integrated in the linker structure and conjugated to $L_2$, $L_3$ lacks the $5^{th}$ amino acid residue (C-terminal G) of the sortase enzyme recognition motifs. In table 1, said C-terminal G is thus shown in parentheses. In case the sortase enzyme recognition motif is a pentapeptide, $L_3$ is thus a tetrapeptide.

Prior to sortase conjugation, the sortase enzyme recognition motifs may furthermore carry other tags, like His-tags, Myc-tags or Strep-tags (see FIG. 4a of WO2014140317, the content of which is incorporated by reference herein), fused C-terminal to the sortase enzyme recognition motifs. However, because the peptide bond between the $4^{th}$ and $5^{th}$ amino acid of the sortase enzyme recognition motif is cleaved upon sortase mediated comjugation, these additional tags will eventually be removed from the fully conjugated BPDC.

The sortase enzyme recognition motifs can be conjugated to the $(Gly)_n$ linker that is conjugated to the anthracycline derivative by means of the sortase technology disclosed herein and in WO2014140317. During the conjugation process, one glycine reside from the $(Gly)_n$ linker is released.

It is noteworthy to mention that, while these three peptide stretches are shown above in the classical N-terminus→C-terminus direction, that the L residue is the one that is fused to the C-terminus of the binding protein, or to the C-terminus of linker Y, by means of a peptide bond. The $5^{th}$ amino acid residue (G) of $L_3$ is removed upon conjugation to the $(Gly)n$ peptide, while the $4^{th}$ T or S amino acid residue of $L_3$ is the one that is actually conjugated to the N-terminus of the $(Gly)n$ peptide.

The following table thus gives an overview of the preferred embodiments of the Binding protein-drug conjugate (BPDC) of the invention, with $L_1$-$L_3$ shown.

TABLE 1

| Typical linker structures | | | | |
|---|---|---|---|---|
| Toxin | $L_1$ | $L_2$ | $L_3$ (shown here C'–> N') | Binding protein |
| formula (i) | alkylene-dieamino group | $(Gly)n$ | (G)TXPL (G)SXPL (G)TXAL | antibody |
| formula (ii) | alkyleneamino group | $(Gly)n$ | (G)TXPL (G)SXPL (G)TXAL | antibody |

As discussed it is noteworthy that, once integrated in the linker structure and conjugated to $L_2$, $L_3$ lacks the $5^{th}$ amino acid residue (C-terminal G). In table 1, said C-terminal G is thus shown in parentheses.

According to another embodiment of the binding protein-drug conjugate (BPDC), the anthracycline (PNU) derivative is conjugated, by means of the one or more linkers, to the carboxy terminus of the binding protein, or to the carboxy termius of a domain or subunit thereof.

In another preferred embodiment, n in the oligo-glycine $(Gly_n)$ peptide linker is an integer between $\geq 3$ and $\leq 11$, more preferably between $\geq 3$ and $\leq 7$, preferably n=3, or n=5. Most preferably, n in the oligo-glycine $(Gly_n)$ peptide linker is 5.

In one preferred embodiment, the payload is the one of formula (i).

In a second preferred embodiment, the payload is the one of formula (ii).

According to another embodiment of the binding protein-drug conjugate (BPDC), the binding protein is conjugated to the free amino terminus of the oligo-glycine peptide ($Gly_n$) by means of an amide bond.

According to another embodiment of the binding protein-drug conjugate (BPDC), the binding protein is at least one selected from the group consisting of an
- antibody,
- modified antibody format,
- antibody derivative or fragment retaining target binding properties
- antibody-based binding protein,
- oligopeptide binder and/or
- an antibody mimetic.

The term "binding protein", as used herein, is equivalent to the term "immunoligand" as used in other publications by the inventors, including the appendix 1, which provides further technical details, disclosure and enablement as regards the sortase enzyme conjugation technology.

"Antibodies", also synonymously called "immunoglobulins" (Ig), are generally comprising four polypeptide chains, two heavy (H) chains and two light (L) chains, and are therefore multimeric proteins, or an equivalent Ig homologue thereof (e.g., a camelid nanobody, which comprises only a heavy chain, single domain antibodies (dAbs) which can be either be derived from a heavy or light chain); including full length functional mutants, variants, or derivatives thereof (including, but not limited to, murine, chimeric, humanized and fully human antibodies, which retain the essential epitope binding features of an Ig molecule, and including dual specific, bispecific, multispecific, and dual variable domain immunoglobulins; Immunoglobulin molecules can be of any class (e.g., IgG, IgE, IgM, IgD, IgA, and IgY), or subclass (e.g., IgG1, IgG2, IgG3, IgG4, IgA1, and IgA2) and allotype.

Provided the binding protein is an antibody, the bind protein drug conjugate is an antibody drug conjugate (ADC).

In the following, ADCs according to this invention are also called "PNU-EDA-$Gly_n$-Ab", "PNU-$Gly_n$-Ab" or "PNU-EA-$Gly_n$-Ab".

An "antibody-based binding protein", as used herein, may represent any protein that contains at least one antibody-derived $V_H$, $V_L$, or $C_H$ immunoglobulin domain in the context of other non-immunoglobulin, or non-antibody derived components. Such antibody-based proteins include, but are not limited to (i) $F_c$-fusion proteins of binding proteins, including receptors or receptor components with all or parts of the immunoglobulin $C_H$ domains, (ii) binding proteins, in which $V_H$ and or $V_L$ domains are coupled to alternative molecular scaffolds, or (iii) molecules, in which immunoglobulin $V_H$, and/or $V_L$, and/or $C_H$ domains are combined and/or assembled in a fashion not normally found in naturally occuring antibodies or antibody fragments.

An "antibody derivative or fragment", as used herein, relates to a molecule comprising at least one polypeptide chain derived from an antibody that is not full length, including, but not limited to (i) a Fab fragment, which is a monovalent fragment consisting of the variable light ($V_L$), variable heavy ($V_H$), constant light ($C_L$) and constant heavy 1 ($C_H1$) domains; (ii) a F(ab')2 fragment, which is a bivalent fragment comprising two Fab fragments linked by a disulfide bridge at the hinge region; (iii) a heavy chain portion of a $F_{ab}$ ($F_d$) fragment, which consists of the $V_H$ and $C_H1$ domains; (iv) a variable fragment ($F_v$) fragment, which consists of the $V_L$ and $V_H$ domains of a single arm of an antibody, (v) a domain antibody (dAb) fragment, which comprises a single variable domain; (vi) an isolated complementarity determining region (CDR); (vii) a single chain $F_v$ Fragment (sc$F_v$); (viii) a diabody, which is a bivalent, bispecific antibody in which $V_H$ and $V_L$ domains are expressed on a single polypeptide chain, but using a linker that is too short to allow for pairing between the two domains on the same chain, thereby forcing the domains to pair with the complementarity domains of another chain and creating two antigen binding sites; and (ix) a linear antibody, which comprises a pair of tandem $F_v$ segments ($V_H$-$C_H1$-$V_H$-$C_H1$) which, together with complementarity light chain polypeptides, form a pair of antigen binding regions; and (x) other non-full length portions of immunoglobulin heavy and/or light chains, or mutants, variants, or derivatives thereof, alone or in any combination. In any case, said derivative or fragment retains target binding properties The term "modified antibody format", as used herein, encompasses antibody-drug-conjugates, Polyalkylene oxide-modified scFv, Monobodies, Diabodies, Camelid Antibodies, Domain Antibodies, bi- or trispecific antibodies, IgA, or two IgG structures joined by a J chain and a secretory component, shark antibodies, new world primate framework+non-new world primate CDR, IgG4 antibodies with hinge region removed, IgG with two additional binding sites engineered into the CH3 domains, antibodies with altered Fc region to enhance affinity for Fc gamma receptors, dimerised constructs comprising CH3+VL+VH, and the like.

The term "antibody mimetic", as used herein, refers to proteins not belonging to the immunoglobulin family, and even non-proteins such as aptamers, or synthetic polymers. Some types have an antibody-like beta-sheet structure. Potential advantages of "antibody mimetics" or "alternative scaffolds" over antibodies are better solubility, higher tissue penetration, higher stability towards heat and enzymes, and comparatively low production costs.

Some antibody mimetics can be provided in large libraries, which offer specific binding candidates against every conceivable target. Just like with antibodies, target specific antibody mimetics can be developed by use of High Throughput Screening (HTS) technologies as well as with established display technologies, just like phage display, bacterial display, yeast or mammalian display. Currently developed antibody mimetics encompass, for example, ankyrin repeat proteins (called DARPins), C-type lectins, A-domain proteins of *S. aureus*, transferrins, lipocalins, $10^{th}$ type III domains of fibronectin, Kunitz domain protease inhibitors, ubiquitin derived binders (called affilins), gamma crystallin derived binders, cysteine knots or knottins, thioredoxin A scaffold based binders, SH-3 domains, stradobodies, "A domains" of membrane receptors stabilised by disulfide bonds and Ca2+, CTLA4-based compounds, Fyn SH3, and aptamers (peptide molecules that bind to a specific target molecules).

The term "oligopeptide binder", as used herein, relates to oligopeptides that have the capacity to bind, with high affinity, to a given target. The term "oligo" refers to peptides that have between 5 and 50 amino acid residues.

According to another embodiment of the binding protein-drug conjugate (BPDC), the binding protein binds at least one entity selected from the group consisting of
- a receptor
- an antigen
- a growth factor,
- a cytokine, and/or
- a hormone.

This list defines the different types of targets the binding protein can bind to. As used herein, the term "receptor" means a cell surface molecule, preferably a cell surface molecule that (i) binds specific, or groups of specific, signaling molecules (i.e. a receptor, like, e.g., the VEGF receptor), and/or (ii) has no known ligand (i.e. an orphan receptor, like, e.g. HER2/neu). The natural receptors are expressed on the surface of a population of cells, or they merely represent the extracellular domain of such a molecule (whether such a form exists naturally or not), or a soluble molecule performing natural binding function in the plasma, or within a cell or organ. Preferably, such receptor is a member of a signaling cascade that is involved in a particular pathogenic process (e.g., a receptor that belongs to a signaling cascade of a growth factor), or is expressed on the surface of a cell or particle that is involved in a pathological process, e.g., a cancer cell.

As used herein, the term "antigen" means a substance that has the ability to induce a specific immune response, and may include surface proteins or protein complexes (e.g. ion channels). Often times, antigens are associated to pathogenic entities, e.g., a cancer cell.

As used herein, the term "cytokine" refers to small cell-signaling protein molecules that are secreted by numerous cells and are a category of signaling molecules used extensively in intercellular communication. Cytokines can be classified as proteins, peptides, or glycoproteins; the term "cytokine" encompasses a large and diverse family of regulators produced throughout the body by cells of diverse embryological origin.

As used herein, the term "growth factor" relates to naturally occurring substances capable of stimulating cellular growth, proliferation and cellular differentiation. Usually a growth factor is a protein or a steroid hormone. Growth factors are important for regulating a variety of cellular processes.

As used herein, the term "hormone" relates to a chemical released by a cell, a gland, or an organ in one part of the body that sends out messages that affect cells in other parts of the organism. The term encompasses peptide hormones, lipid and phospholipid-derived hormones including steroid hormones, and monoamines.

In case the binding protein binds a receptor or an antigen, the binding protein-drug conjugate (BPDC) can for example be directed to a specific site, e.g., to a pathogenic entity, e.g., a cancer cell, where the payload, e.g. a toxin is delivered. Thus, the systemic toxicity of the toxin or the chemotherapeutic agent is reduced, while the local concentration of the latter at the site of action is increased, thus providing a better efficacy while side effects are reduced. Furthermore, a respective signaling cascade can be inhibited by the binding of the binding protein. In case the payload is a marker the latter can thus be used to mark a specific site, e.g., a cancer cell characterized by a given surface antigen detected by the binding protein, for diagnosis.

In case the binding protein binds a growth factor, a cytokine, and/or a hormone, the binding protein-drug conjugate (BPDC) can for example be directed to the site the growth factor cytokine or hormone usually binds to, in order to deliver the payload in a site-specific manner. Further, a respective signaling cascade can be inhibited by the binding of the binding protein.

As used herein, the term "to bind" means the well-understood interaction or other nonrandom association between binding protein, e.g., antibodies, or antibody fragments, and their targets. Preferably, such binding reaction is characterized by high specificity and/or sensitivity to the target. Preferably, the binding reaction is characterized by a dissociation constant (Kd)≤$10^{-3}$ M, preferably ≤$10^{-4}$ M, ≤$10^{-5}$ M, ≤$10^{-6}$ M, ≤$10^{-7}$ M, ≤$10^{-8}$ M, ≤$10^{-9}$ M, and most preferred ≤$10^{-10}$.

According to another embodiment, the binding protein has at least two subunits.

In this embodiment, one subunit can be conjugated to a derivative of the anthracycline PNU-159682 disclosed herein (see FIGS. 3A and 6A and 6B).

Preferably, at least two different drugs can be conjugated to the at least two subunits site-specifically. This option provides a versatile toolbox with which a large variety of different binding protein-drug constructs can be created.

Preferably, the at least two different drugs are drugs interfering with different cellular pathways. This means that, next to the anthracycline derivative conjugate disclosed herein, a second toxin can be conjugated to another subunit of the same binding protein.

Such embodiment can be accomplished, e.g., by conjugating the two different drugs to each the 2 light chains of a full-length antibody, and to the 2 heavy chains of a full length antibody, respectively, by utilizing two different sortase enzymes, recognizing different sortase recognition motifs ("sortase tags"), plus an antibody that contains different C-terminal modifications at heavy and light chains comprising the respective recognition motifs for said different sortase enzymes.

In such way, an Antibody Drug Conjugate can be created which is composed of each two full-length Ig light chains and Ig heavy chains, containing different payloads covalently attached to said heavy and light chains.

Such embodiment results, preferably, in the site-specific conjugation of the at least two subunits for the generation of binding protein drug conjugates with site-specific and equal payload conjugation to each of said subunits.

In one embodiment of the binding protein-drug conjugate (BPDC) the binding protein binds HER-2. Preferably, the binding protein is an antibody specific for HER-2.

In this embodiment, the HER-2 specific antibody preferably
a) comprises the CDR regions 1-6 of trastuzumab (humanized hu4D5)
b) comprises the heavy chain variable domain and the light chain variable domain of trastuzumab
c) has an amino acid sequence identity of 90% or higher with the regions or domains of a) or b)
d) is trastuzumab, or a target binding fragment or derivative thereof, and/or
e) competes with trastuzumab for binding to Her-2

The anti-HER-2 monoclonal antibody trastuzumab binds to domain IV of HER-2. Preferably, the anti-HER-2 antibody comprises the primary amino acid sequences of IgH and IgL chains of FIG. 11A (Seq ID Nos 1 and 2). The sequences of trastuzumab are also disclosed in drug bank accession number DB00072 (BIOD00098, BTD00098), which is incorporated by reference herein, as well as in the IMGT database (VH: http://www.imgt.org/3Dstructure-DB/cgi/details.cgi?pdbcode=7637&Part=Chain&Chain=7637H & VL: http://www.imgt.org/3Dstructure-DB/cgi/details.cgi?pdbcode=7637&Part=Chain&Chain=7637L).

In another embodiment of the binding protein-drug conjugate (BPDC) the binding protein binds CD30. Preferably, the binding protein is an antibody specific for CD30.

In this embodiment, the antibody preferably
a) comprises the CDR regions 1-6 of brentuximab (chimeric cAc10)

b) comprises the heavy chain variable domain and the light chain variable domain of brentuximab
c) has an amino acid sequence identity of 90% or higher with the regions or domains of a) or b)
d) is brentuximab or a target binding fragment or derivative thereof, and/or
e) competes with brentuximab for binding to CD30

The sequences of Brentuximab (clone cAc10), which is the antibody component of the approved drug Adcetris/Brentuximab vedotin is disclosed in US2008213289A1.

Figure 11A:
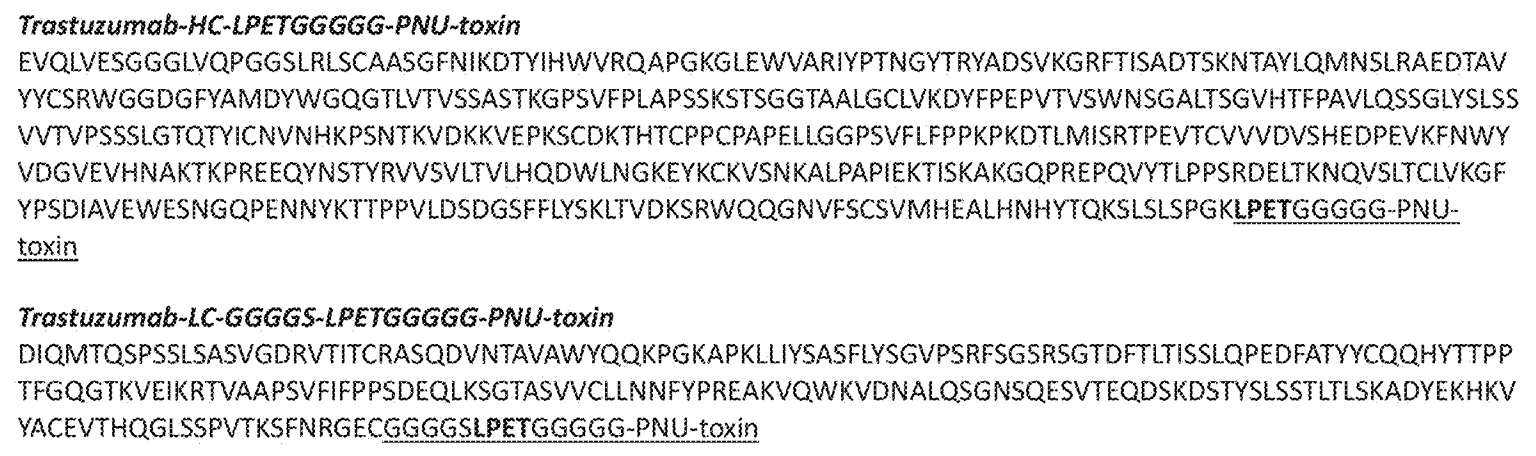
Figure 11B:
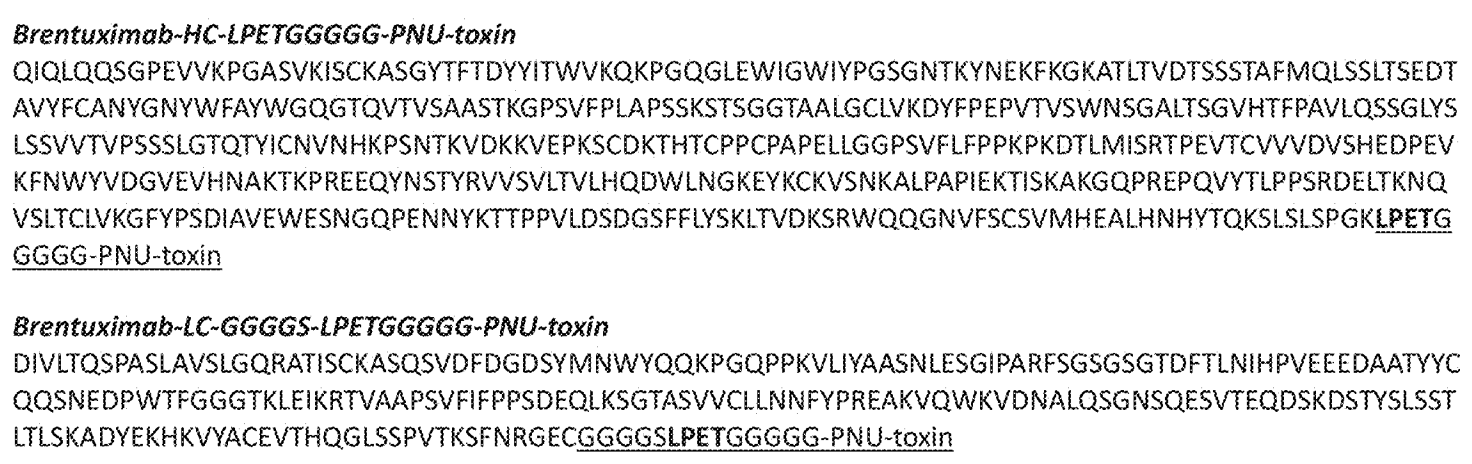

Preferably, the anti-CD30 antibody comprises the primary amino acid sequences of IgH and IgL chains of FIG. 11B (Seq ID Nos 3 and 4).

Preferably, in these embodiments, the toxin is the one of formula (i),
$L_1$ is an ethylendiamino linker,
$L_2$ is an oligo-glycine $(Gly_n)$ peptide linker (with n being the preferred length of 5 amino acids), and
$L_3$ represents the amino acid residues 1-4 of a processed sortase tag pentapeptide motif (i.e., devoid of the C-terminal G residue ($5^{th}$ amino acid residue), which removed upon sortase mediated conjugation to the $(Gly)n$ peptide,
Linker X is absent, and
Y is a 5 amino acid linker between the C-terminus of the Ig light chain and L3, having preferably the amino acid sequence GGGGS.
Alternatively, the toxin is the one of formula (ii), while
L1 is an ethylenamino linker,
L2 is an oligo-glycine $(Gly_n)$ peptide linker, (with n being the preferred length of 5 amino acids),
$L_3$ represents the amino acid residues 1-4 of a processed sortase tag pentapeptide motif (i.e., devoid of the C-terminal G residue ($5^{th}$ amino acid residue), which removed upon sortase mediated conjugation to the $(Gly)n$ peptide,
Linker X is absent, and
Y is a 5 amino acid linker between the C-terminus of the Ig light chain and L3, having preferably the amino acid sequence GGGGS.

The invention further provides a method of producing a binding protein-drug conjugate (BPDC) according to the above description, wherein a binding protein carrying a sortase enzyme recognition motif is conjugated, by means of a sortase enzyme, to at least one anthracycline derivative conjugate which carries, as $L_2$, an oligo-glycine peptide $(Gly_n)$.

The sortase technology, its advantages (site specific conjugation, stoichimetrically defined relationship between toxin and binding protein, high efficiency of conjugation) is in detail explained in application WO2014140317A1, the content of which is incorporated by reference herein. Further explanations with respect to the sortase tags are found above, It is a preferred embodiment of the present invention to conjugate PNU-derivative payloads by SMAC technology to the C-terminus of binding proteins, and preferably to the C-terminus of antibody or immunoglobulin chains to at least one Ig light or Ig heavy chain. This is achieved by generating mammalian cell expression constructs for binding protein or immunoglobulin subunits which encode for a C-terminal pentapeptide recognition motif for sortase enzymes directly following the C-terminus of the binding protein, or the polypeptide subunit of a multimeric binding protein, like e.g. an antibody.

It is to be understood that the pentapeptide motif of sortase A of *Staphylococcus aureus*, which is LPXTG or LPXSG and which has been mentioned before, is only provided as a non-limiting example and may be replaced by any other pentapeptide motif recognized by sortase enzymes from other species or other classes, like sortase B from *Staphylococcus aureus*, which recognizes the pentapeptide motif NPQTN. Also recognition motifs may be used that are recognized by engineered sortase enzymes, like e.g. LAETG, recognized by an engineered version of sortase A of *Staphylococcus aureus* recently described by Dorr et al. (2014).

WO2014140317 further provides technical details, disclosure and enablement with regard to the sortase conjugation technology, which is also called SMAC technology (sortase mediated antibody conjugation technology). This technology allows the conjugation of two entities, one marked with a $(Gly)_n$ stretch (as discussed for the toxin above herein) and one with a so-called sortase tag, which is a peptide tag than can be attached, e.g., to a binding protein.

These sortase tags are oligopeptides, usually pentapeptide motifs, which are fused to a first entity (here: the binding protein) that is to be conjugated to a second entity (here: the anthracyclin derivative), in such way that the C-terminus of said sortase tags oligopeptides remains free. As disclosed in WO2014140317 this can be accomplished by expressing the binding proteins from expression vectors encoding the additional amono acids for the pentapeptide sortase tag.

Such sortase tag is e.g, LPXTG or LPXSG (for sortase A from *Staphylococcus aureus*), LPXSG (for engineered sortase A 4S9 from *Staphylococcus aureus* described in Dorr et al., 2014), or LAXTG (for engineered sortase A 2A9 from *Staphylococcus aureus* described in Dorr et al., 2014) with X being any of the 20 naturally occuring amino acids. However, such sortase tags may differ in sequence for sortase enzymes from other bacterial species or for sortase classes, as disclosed in WO2014140317, and in the prior art (Spirig et al. 2011).

The second entity comprises a Glycine-stretch $(Gly_n$-stretch) with a free N-terminus ($—NH_2$), which $Gly_n$-stretch is an oligo-glycine peptide. Preferably, n is an integer between $\geq 1$ and $\leq 21$. In one particularly preferred embodiment, n is an integer between $\geq 3$ and $\leq 10$, preferably n=3 or n=5. Most preferred, n=5.

The sortase enzyme is then capable of fusing the two entities to one another by means of a transpeptidation reaction, during which the C-terminal amino acid residue (e.g., the G in LPXTG) is cleaved of, and then replaced by the first glycine of said glycine stretch.

In another preferred embodiment the pentapeptide recognition motif may directly be appended to the last naturally occurring C-terminal amino acid of the immunoglobulin light chains or heavy chains, which in case of the human immunoglobulin kappa light chain is the C-terminal cysteine residue, which in case of the human immunoglobulin lambda light chain is the C-terminal serine residue and which in the case of the human immunoglobulin $IgG_1$ heavy chain may be the C-terminal lysine residue encoded by human Fcγ1 cDNA. However, another preferred embodiment is also to directly append the sortase pentapeptide motif to the second last C-terminal glycine residue encoded by human Fcγ1 cDNA, because usually terminal lysine residues of antibody heavy chains are clipped off by prosttranslational modification in mammalian cells. Therefore, in more than 90% of the cases naturally occurring human IgG1 lacks the C-terminal lysine residues of the IgG1 heavy chains.

In another preferred embodiment the pentapeptide recognition motif may be appended to the C-terminus of a human immunoglobulin IgG$_1$ heavy chain where the C-terminal lysine residue encoded by human Fcγ1 cDNA is replaced by an amino acid residue other than lysine.

We have described previously that in some cases (e.g. at the C-terminus of the Ig kappa light chains, (Beerli et al. 2015) it is beneficial to add additional amino acids between the C-terminus of the binding protein and the sortase tag, L$_3$. This has been shown to improve sortase enzyme conjugation efficiencies of payloads to the binding protein. In the case of Ig kappa light chains, it was observed that by adding 5 amino acids (GGGGS) between the last C-terminal cysteine amino acid of the Ig kappa light chain and the sortase tag improved the kinetics of conjugation, so that the C-termini of Ig kappa light chains and Ig heavy chains could be conjugated with similar kinetics (see: Beerli et al. (2015). Therefore, it is another preferred embodiment to optionally include a linker Y of between ≥1 and ≤21 amino acids in between the last C-terminal amino acid of a binding protein or antibody subunit and the sortase tag, L$_3$.

The invention further provides the use of a binding protein drug conjugate (BPDC) according to the above description, or produced with a method of the above description, for the treatment of a human or animal subject
  suffering from,
  at risk of developing, and/or
  being diagnosed for
a given pathologic condition.

The invention further provides the use of a binding protein drug conjugate according to the above description for the manufacture of a medicament for the treatment of a human or animal subject
  suffering from,
  at risk of developing, and/or
  being diagnosed for
a given pathologic condition.

Preferably, the pathologic condition is a neoplastic disease. More preferably, the neoplastic disease is
  a cancer that has an HER-2 expression score of 1+, 2+ or 3+, as determined by IHC or ISH, which cancer is preferably a breast cancer
  a cancer that is CD30 positive as determined by IHC, ELISA or flow cytometry, preferably a lymphoma, more preferably a Hodgkin lymphoma (HL) or a systemic anaplastic large cell lymphoma (sALCL)

Determination of the HER-2 status can for example be determined according to the ASCO/CAP guidelines, which are described in Wolff et al 2013.

Determination of the CD30 status can for example be determined according to the method of Young 2014.

The invention further provides a pharmaceutical composition comprising a binding protein drug conjugate (BPDC) according to the above description, or produced with a method of the above description, and at least one other pharmaceutically acceptable ingredient.

Further Description

In order to overcome the main limitations of traditional maleimide linker chemistry for the generation of BPDCs and ADCs, we have previously developed an enzymatic approach for generating BPDCs or ADCs using sequence-specific transpeptidase enzymes, either employing sortase enzymes, or so-called split-inteins (see: WO2014140317A1). In particular, it could be demonstrated that site-specific conjugation of small molecular payloads by sortase enzymes, in the context of antibodies, referred to as SMAC-technology (sortase-mediated antibody conjugation technology), results in ADCs that are equally potent as chemically conjugated ADCs in killing cancer cells in vitro, if the same binding protein and the same payload is employed, Furthermore, SMAC-technology generated ADCs specific for the HER-2 target lead to similarly potent tumor regression in xenotransplantation models, if the same targeting antibody (anti-HER-2 trastuzumab) and the same toxic payload (DM1) was employed (WO2014140317A1). However, first, in SMAC-generated ADCs no maleimide linker chemistry was employed, and second, the conjugation reaction was performed in a site-specific manner to the C-termini of either IgH or IgL chains of the antibody, so that more homogeneous ADCs have been obtained.

In case of SMAC-technology, the site-specific conjugation can be effected by e.g. recombinant sortase A enzyme of *Staphylococcus aureus*, that specifically recognizes an LPXTG or LPXSG pentapeptide motif (X=any of the 20 naturally occuring amino acids) and that can be appended to a recombinant antibody intended for conjugation. Sortase A then uses an oligo-glycine-stretch as a nucleophile to catalyze a transpeptidation, by which the amino group of the oligo-glycine effects a nucleophilic attack to the peptide bond between the threonine or serine and glycine of the LPXTG or LPXSG pentapeptide motif. This results in the breakage of that peptide bond and the formation of a new peptide bond between the N-terminal glycine of the oligo-glycine peptide (see FIG. 1), i.e. resulting in a transpeptidation.

While it has been shown that trastuzumab-DM1 conjugates generated by sortase-mediated conjugation have comparable potency to the chemically conjugated DM1 conjugates (T-DM1, or Kadcyla®, already applied in the clinic), higher potency of SMAC-technology generated ADCs has not been achieved (WO2014140317A1). This would not have been expected, because the same targeting antibody and the same payload have been employed.

Based on this and also other experiments with different monoclonal antibodies specifically binding to other TSAs, that are potentially expressed at lower levels on cancer cells than the HER-2 target, or that are potentially less efficiently internalized upon ADC binding (data not show), it became apparent, that toxic payloads with higher potency than maytansines, and/or with a potentially different mode of action are required to produce sufficiently effective ADCs. In addition, the payload has to be amenable to modification at least one reactive group, allowing the addition of an oligo-glycine peptide to enable sortase conjugation of the payload to LPXTG- or LPXSG-modified binding proteins. Lastly, if higher potency toxins are employed, the modification should result in a stable linkage between the glycine-stretch and the payload, in order to prevent undesired release of the toxic payload in circulation, but at the same time the toxin should still result in effective killing of cancer cells upon specific binding and internalization of the BPDC or ADC into tumor cells.

Empiric evaluation of different toxic payloads described in the prior art in the context of SMAC-technology has resulted in the finding that a highly potent anthracycline derivative of nemorubicin, called PNU-159682 (Quintieri et al., 2005) (see also FIG. 2), that has been modified with an ethylenediamine-spacer, in order to allow addition of a pentaglycine stretch could very efficiently be conjugated to LPXTG modified antibodies by SMAC technology yielding almost completely conjugated ADCs based on analyses of the products by HIC (hydrophobic interaction chromatography) and reverse-phase chromatography (data not shown). In addition, if this modified PNU-159682 derivative, termed PNU-EDA-Gly$_5$, is SMAC conjugated to various monoclonal antibodies, as described in the EXAMPLES, provided below, highly potent and TSA-dependent killing of tumor cells has been effected. In particular, HER-2 low expressing human breast cancer cells could efficiently be killed in vitro with SMAC-technology conjugated PNU-EDA-Gly$_5$, conjugates, whereas maytansine-toxin conjugates were hardly effective. This demonstrates the potential utility of the PNU-EDA-Gly$_5$ derivative for generating potent BPDCs and ADCs, preferably containing PNU-EDA-Gly$_5$, or any PNU-derivative with a oligo-glycine peptide with at least two glycines attached to it. In addition, it demonstrates the utility of BPDCs and ADCs containing preferably PNU-EDA-Gly$_5$, or any PNU-derivative with a oligo-glycine peptide as the payload for the treatment of cancer diseases.

Although anthracycline derivative PNU-159682 (FIG. 2) and its use in the context of chemical conjugation and ADCs have been described in the prior art (e.g. WO2009099741A1, WO2010009124, WO2012073217, provided for reference herein), a compound similar to PNU-EDA-Gly$_n$, or ADCs containing sortase-conjugated PNU-EDA-Gly$_n$, as disclosed herein, have not yet been described in the prior art, nor is the particular structure of the PNU-derivative with EDA spacer and Gly$_n$ linker disclosed or claimed in any of the prior art documents. Stable adducts, in which PNU derivatives are stably linked to proteins via peptide bonds rather than by ester bonds and maleimide linkers may prove to be superior, in terms of stability and pharmacokinetic behavior in vivo, due to a generally high stability of peptide bonds in serum, as disclosed in the Examples further below. Additionally, PNU-derivatives with Gly$_n$-stretch that are expected to display stable drug conjugates after SMAC-technology conjugation are disclosed in FIG. 6A and FIG. 6B.

Experiments and Figures

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

All amino acid sequences disclosed herein are shown from N-terminus to C-terminus; all nucleic acid sequences disclosed herein are shown 5'→3'.

Example 1

Generation of Site-Specifically C-Terminally PNU-EDA-Gly$_n$-Payload Conjugated Monoclonal Antibodies Brentuximab and Trastuzumab by Sortase Mediated Antibody Conjugation Technology (SMAC-Technology)

The heavy and light chain variable region sequences of monoclonal antibody brentuximab (clone cAc10) specific for the human CD30 target were obtained from patent US2008213289A1, those of the human HER-2 specific trastuzumab antibody contained in the commercial antibody Herceptin (trastuzumab), or the ADC Kadcyla® derived thereof, were derived from the online IMGT database (VH: http://www.imgt.org/3D structure-DB/cgi/details.cgi?pdbcode=7637&Part=Chain&Chain=7637H & VL: http://www.imgt.org/3Dstructure-DB/cgi/details.cgi?pdbcode=7637&Part=Chain&Chain=7637L. Chimeric mAb cAc10 and humanized mAb trastuzumab were produced with their heavy and light chains C-terminally tagged with a Sortase A recognition sequence and an additional Strep II affinity purification tag (HC tag sequence: LPETGGWSHPQFEK; LC tag sequence: GGGGS LPETGGWSHPQFEK) using methods known to those skilled in the art. (see FIGS. 11A & 11B).

The anthracycline derivative PNU-EDA-Gly$_5$ (FIG. 3A) was provided by Levana Biopharma, San Diego, Calif., which synthesized a pentaglycin peptide to the carbonyl group of PNU159682 via an ethylenediamino (EDA) linker according to the synthesis scheme of FIG. 3B. For this, commercially available PNU159682 was first oxidized to obtain a carboxylic acid thereof (1 on FIG. 3B) with NaIO$_4$ in 60% methanol at RT for 3 hours. Thereafter, N-hydroxysuccidimide (NHS, 46 mg, 400 µmol) and ethyl(dimethylaminopropyl) carbodiimide (EDC, 100 mg, 523 µmol) in dichloromethane (DCM) were added to a solution of 1(51 mg, 81 µmol) in 6 mL of DCM. After 30 min, the mixture was washed with water (2×6 mL), dried over Na$_2$SO$_4$ and evaporated. The residue was then dissolved in 2 mL of dimethylformamide (DMF) prior to addition of the amine (2 on FIG. 3B, 55 mg, 81 µmol, as trifluoroacetate salt), followed by addition of N,N-diisopropylethylamine (DIEA, 50 µL). The mixture was stirred for 1 h prior to addition of piperidine (40 µL), followed by 20 min of additional stirring. The mixture was purified by HPLC to give PNU-EDA-Gly$_5$ (3 on FIG. 3B, 34 mg, 44%) as a red solid; MS m/z 955.2 (M+H).

PNU-EDA-Gly$_5$ was conjugated to mAbs by incubating LPETG-tagged mAbs [10 µM] with PNU-EDA-Gly$_5$, [200 µM] in the presence of 0.62 µM Sortase A in 50 mM Hepes, 150 mM NaCl, 5 mM CaCl$_2$, pH 7.5 for 3.5 h at 25° C. The reaction was stopped by passing it through a Protein A HiTrap column (GE Healthcare) equilibrated with 25 mM sodium phosphate pH 7.5, followed by washing with 5 column volumes (CVs) of buffer. Bound conjugate was eluted with 5 CVs of elution buffer (0.1M succinic acid, pH 2.8) with 1 CV fractions collected into tubes containing 25% v/v 1M Tris Base to neutralise the acid. Protein containing fractions were pooled and formulated in 10 mM Sodium Succinate pH 5.0, 100 mg/mL Trehalose, 0.1% % w/v Polysorbate or phosphate20 by G25 column chromatography using NAP 25 (GE Healthcare) columns according to the manufacturer's instructions.

The aggregate content of each conjugate was assessed by chromatography on a TOSOH TSKgel G3000SWXL 7.8 mm×30 cm, 5 µm column run at 0.5 mL/min in 10% IPA, 0.2M Potassium Phosphate, 0.25M Potassium Chloride, pH 6.95. The drug loading was assessed both by Hydrophobic Interaction Chromatography (HIC) and Reverse-Phase Chromatography. HIC was performed on a TOSOH Butyl-NPR 4.6 mm×3.5 cm, 2.5 µm column run at 0.8 mL/min with a 12 minute linear gradient between A-1.5M (NH$_4$)$_2$SO$_4$, 25 mM NaPi, pH=6.95±0.05 and B-75% 25 mM NaPi, pH=6.95±0.05, 25% IPA. Reverse phase chromatography was performed on a Polymer Labs PLRP 2.1 mm×5 cm, 5 µm column run at 1 mL/min/80° C. with a 25 minute linear gradient between 0.05% TFA/H$_2$O and 0.04% TFA/CH$_3$CN. Samples were first reduced by incubation with DTT at pH 8.0 at 37° C. for 15 minutes. Both PNU-EDA-Gly$_5$-based ADCs were predominantly monomeric and had drug-to-antibody-ratios close to the theoretical maximum of, respectively, 4. Table 2 summarizes the results of the ADC manufacturing.

TABLE 2

Summary of PNU-EDA-Gly$_5$-based ADCs manufactured.
HC, heavy chain; LC, light chain; % mono, % monomer content; DAR, drug-to-antibody-ratio.

| mAb | target | HC tag | LC tag | % mono | DAR |
|---|---|---|---|---|---|
| Brentuximab | CD30 | Yes | Yes | 99.6 | 4.0 |
| Trastuzumab | HER-2 | Yes | Yes | 98.2 | 3.9 |

Example 2

Figure 4A:
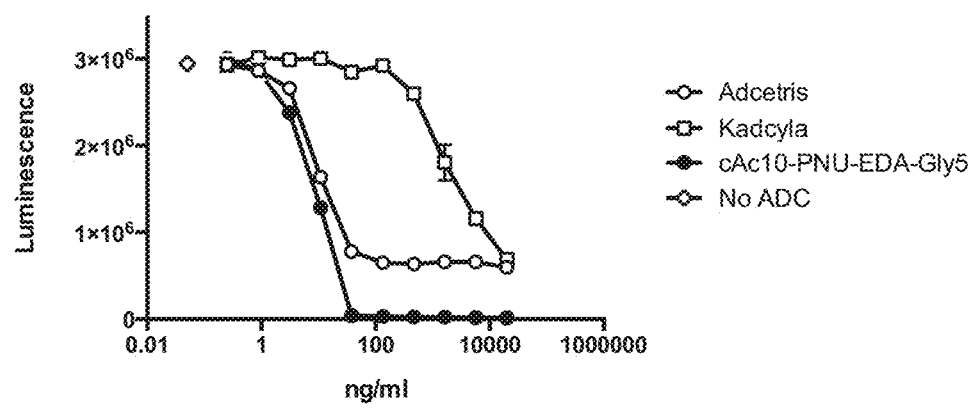
Figure 4B:
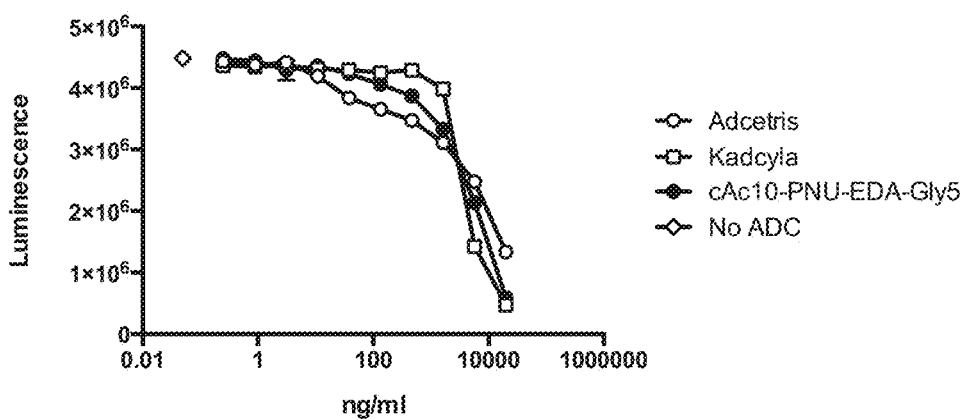

In Vitro Cytotoxicity Assay with Sortase A-Conjugated Brentuximab-PNU-EDA-Gly$_5$ and Trastuzumab-PNU-EDA-Gly$_5$ ADCs Cytotoxicity of Brentuximab-PNU-EDA-Gly$_5$ was investigated using Karpas-299, a non-Hodgkin's lymphoma cell line expressing high levels of CD30, and L428, a Hodgkin's lymphoma cell line expressing low to moderate levels of CD30 (FIGS. 4A and 4B). As controls, efficacy of cAc10-PNU-EDA-Gly$_5$ was compared to that of the commercially available CD30-specific cAc10-vcPAB-MMAE conjugate Adcetris® (as positive control) and the commercially available HER-2-specific Trastuzumab-DM1 conjugate Kadcyla® (as negative control). For this, cells were plated on 96-well plates in 100 µl RPMI/10% FCS at a density of 10$^4$ cells per well and grown at 37° C. in a humidified incubator at 5% CO$_2$ atmosphere. After one day incubation, 25 µl medium was carefully removed from each well and replaced by 25 µl of 3.5-fold serial dilutions of each ADC in growth medium, resulting in final ADC concentrations ranging from 20 µg/ml to 0.25 ng/ml. Each dilution was done in duplicate. After 4 additional days, plates were removed from the incubator and equilibrated to room temperature. After approximately 30 minutes, 100 µl CellTiter-Glo® Luminescent Solution (Promega, Cat. No G7570) was added to each well and, after shaking the plates at 450 rpm for 5 min followed by a 10 min incubation without shaking, luminescence was measured on a Tecan Infinity F200 with an integration time of 1 second per well.

As expected, the anti-CD30 ADC Adcetris® used as a positive control potently killed CD30$^{HI}$ Karpas-299 cells with an EC50 of 8.2 ng/ml (FIG. 4A), while being inefficient at killing CD30$^{LO}$ L428 cells (FIG. 4B). In contrast, the anti-HER-2 ADC Kadcyla® used as a negative control displayed no specific cell killing and was ineffective on either cell line (FIGS. 4A and 4B). Significantly, Sortase-conjugated ADC cAc10-PNU-EDA-Gly$_5$ potently killed the CD30$^{HI}$ Karpas-299 cells with an EC50 value of 6.9 ng/ml (FIG. 4A). cAc10-PNU-EDA-Gly$_5$ killed the CD30$^{LO}$ L428 cells only at higher concentrations, similar to the control ADCs employed, indicating that the efficacy of this ADC is indeed specific and mediated by CD30 binding (FIG. 4B). Thus, Sortase-mediated conjugation of PNU-EDA-Gly$_5$ yielded an ADC with a very high potency, even exceeding that of the reference ADC Adcetris®.

Figure 5A:
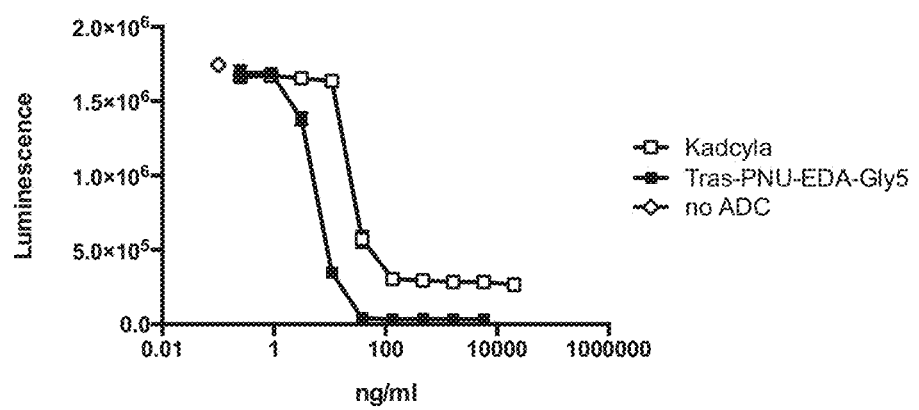
Figure 5B:
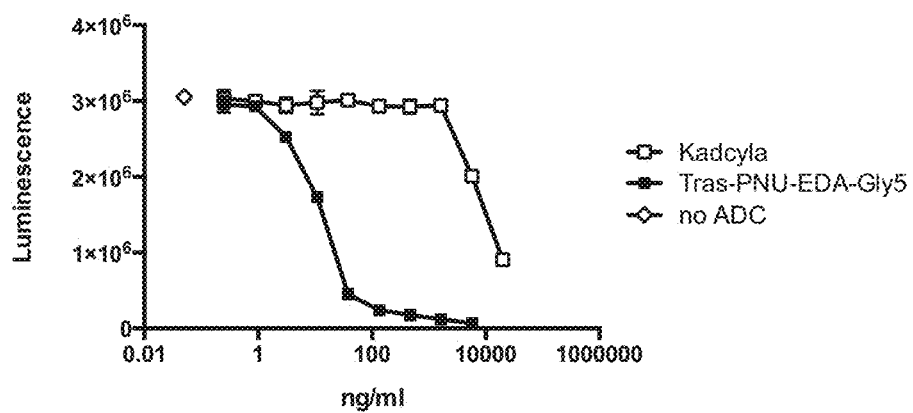

The potency for tumor cell killing of a SMAC-generated Trastuzumab-PNU-EDA-Gly$_5$ ADC was investigated using SKBR3 cells, a human breast cancer cell line overexpressing HER-2, and T47D cells, a breast cancer cell line naturally expressing low levels of HER-2, and this was compared to the commercially available HER-2-specific ADC Trastuzumab-DM1 conjugate Kadcyla® (FIGS. 5A and 5B). For this, cells were plated on 96 well plates in 100 µl DMEM/10% FCS at a density of 10$^4$ cells per well and assays were performed exactly as described above.

As expected, the positive control ADC Kadcyla® potently killed HER-2-overexpressing human SKBR3 breast cancer cells, with an EC50 of 23.7 ng/ml (FIG. 5A), while being ineffective at killing HER-2$^{LO}$ T47D cells (FIG. 5B). Significantly, Trastuzumab-PNU-EDA-Gly$_5$ generated by SMAC-technology displayed superior cytotoxicity and not only killed HER-2-overexpressing SKBR3 cells, but also HER2$^{LO}$ T47D cells, with EC50 values of, respectively, 4.8 and 11.0 ng/ml (FIGS. 5A and 5B). Thus, Sortase-mediated conjugation of PNU-EDA-Gly$_5$ to Trastuzumab yields an ADC with a very high potency, exceeding that of the commercially available and FDA-approved reference ADC Kadcyla®, and is even effective on HER2$^{LO}$ human breast cancer cells.

Example 3

In Vitro Serum Stability of Sortase A-Conjugated cAc10-PNU-EDA-Gly$_5$ ADC as Compared to Maleimide Linker Containing Trastuzumab Emtansine (Kadcyla®)

The in vitro serum stability of brentuximab-PNU-EDA-Gly$_5$ (cAc10-PNU-EDA-GLY$_5$) and Kadcyla ADCs was evaluated in an ELISA-based serum stability assay. Briefly, cAc10-PNU-EDA-Gly$_5$ was diluted in mouse (Sigma, M5905), rat (Sigma, R9759) and human serum (Sigma, H6914), and incubated at 37° C. Samples were snap-frozen in liquid nitrogen on days 0, 3, 7, 14 and stored at −80° C. until ELISA analysis. For rodent sera, dilution series of cAc10-PNU-EDA-Gly$_5$ serum samples were captured on ELISA plates coated with 2 µg/ml of a mouse anti-PNU mAb (produced in-house by immunizing mice with a human IgG-PNU conjugate and screening with a BSA-PNU conjugate) to bind ADC, or with anti-human Fc F(ab')2 (Jackson Immunoresearch) to bind total IgG, and detected with a 1:2500 dilution of an HRP-conjugated anti-human IgG F(ab')2 (Jackson Immunoresearch). For primate sera, 2 µg/ml of recombinant human CD30 (Sino Biologicals, 10777-H08H) was coated on ELISA plates and a 1:2500 dilution of HRP-conjugated anti-human IgG F(ab')2 (Jackson Immunoresearch) or 1 µg/ml of a mouse anti-PNU IgG (produced in-house) followed by HRP-conjugated anti-mouse Fc F(ab')2 (Jackson Immunoresearch) was used for detection of total IgG and ADC, respectively. In the case of Kadcyla, the same protocol was used as above to determine stability in mouse, rat and human serum but with an in-house produced anti-maytansine mAb to bind ADC. Serum concentrations of ADC and total IgGs were calculated from half maximal values of the sample titrations by comparison with a sample of the same ADC of known concentration.

Figure 7A:
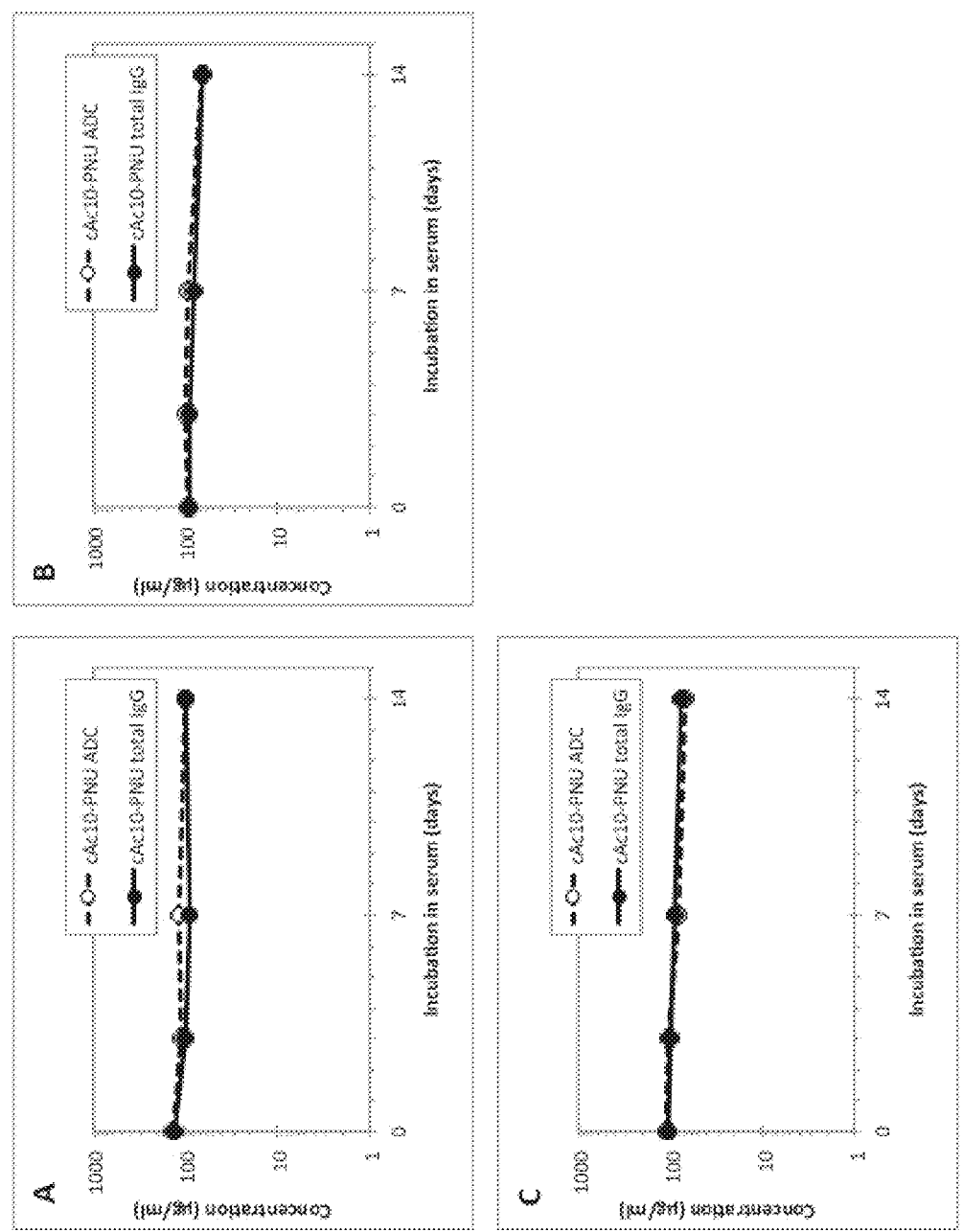
Figure 7B:
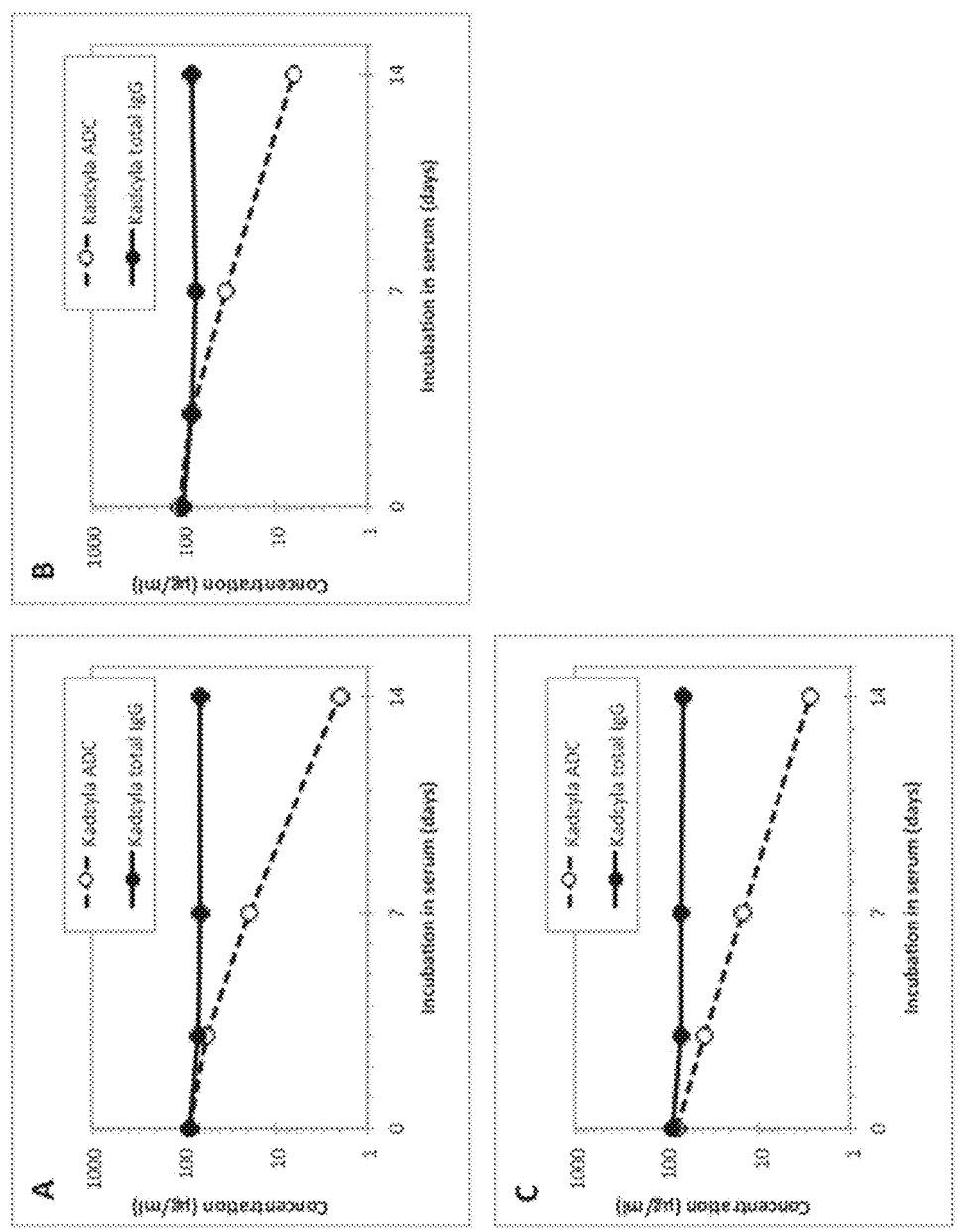

FIGS. 7A and 7B show the excellent stability of cAc10-PNU-EDA-Gly$_5$ ADC, particularly as compared to that of maleimide linker containing Kadcyla (FIG. 7B), with virtually no decrease in ADC levels throughout the entire experiment in any serum of the four species tested. By fitting the time points between day 0 and 14 to a one-phase exponential decay function constrained to reach a final concentration of 0, the half-life values of cAc10-PNU-EDA-Gly$_5$ and Kadcyla were determined in each serum. The half-life of Kadcyla was of 3.7 days, 4.4 days and 2.9 days in mouse, rat and human serum, respectively, whereas the half-life of cAc10-PNU-EDA-Gly$_5$ was greater than 14 days in mouse, rat and human serum.

Example 4

In Vivo Stability of Sortase A-Conjugated Ac10-Gly5-PNU in Mice

Ac10-Gly5-PNU ADC was thawed at room temperature and diluted to 0.2 mg/ml in sterile PBS for a dosing concentration of 1 mg/kg. The samples were injected i.V. at a volume of 5 mL/kg in nine female Swiss Webster mice. Blood was collected from animals after 1 h, 24 h, 72 h, 7 days, 14 days, and 21 days. Individual animals according to ethical standards were only used for two blood draw time points at least a week apart. Thus, three mice had blood drawn after 1 h and 7 days, three different mice had blood drawn after 24 h and 14 days, and three additional different mice had blood drawn after 72 h and 21 days for a total of nine mice per group. For each group of animals, approximately 200 µL of blood was collected by lancet-puncture of the submandibular vein during the first collection, and approximately 600 µL of blood by lancet-puncture of submandibular vein during the final collection (terminal bleed). All blood was collected into tubes containing K2-EDTA. Plasma was isolated from blood by centrifugation at 1500 g for 10 minutes, and transferred to sterile cryovials for storage at −80° C. until analysis by ELISA as described in Example 4.

Figure 8:
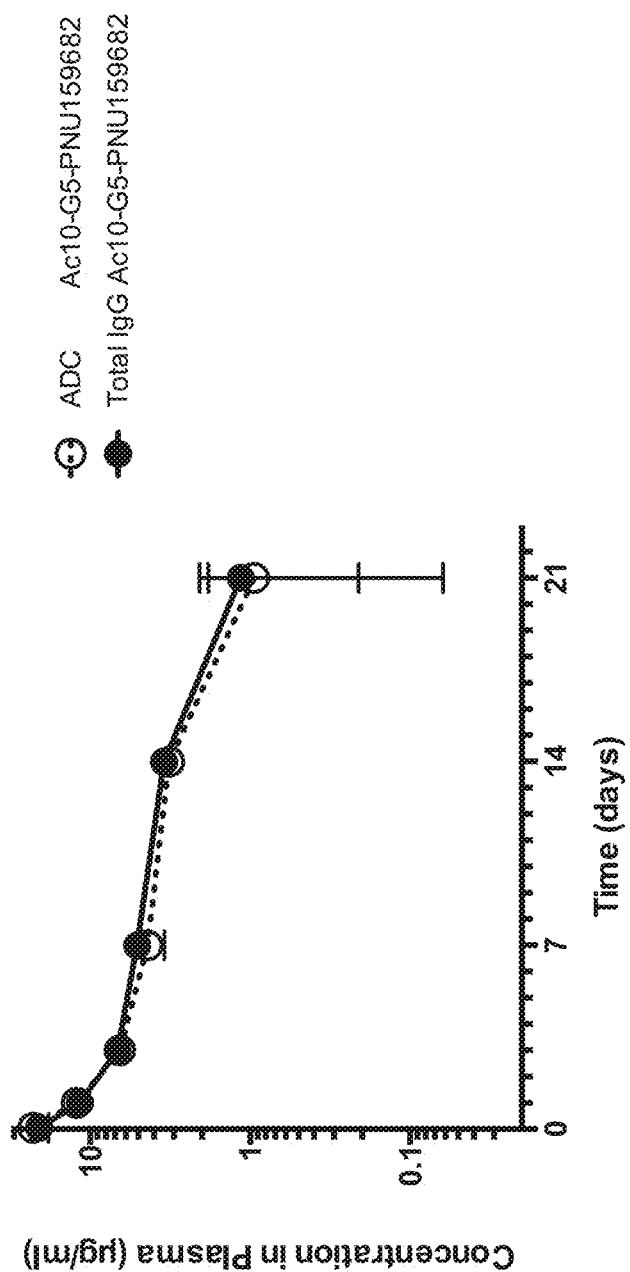

The data in FIG. 8 shows the high stability of the ADC generated by SMAC-technology. For the entire duration of the experiment, concentrations of ADC are only marginally lower than those measured for total IgG, which implies that the linker between drug and antibody is stable in vivo. By fitting the time points between day 3 and 21 to a one-phase exponential decay function constrained to reach a final concentration of 0, in vivo half life in the slow phase was determined with 8.3 and 7.8 days for total IgG and ADC, respectively.

Example 5

Description and Characterization of EMT-6 Clones Expressing HER-2

Cytotoxicity of anti-HER-2 ADCs was investigated using the murine mammary tumor cell line EMT-6 engineered to overexpress human HER-2. EMT-6 cells were cultured as monolayers in DMEM (Dulbecco's Modified Eagle Medium-high glucose) supplemented with 10% (v/v) of FCS (Fetal Calf Serum), 1% (v/v) of 10,000 IU/mL penicillin-streptomycin and 1% (v/v) of 200 mM L-glutamine.

EMT-6 cells were electroporated with an expression vector encoding the human HER-2 gene and a puromycin resistance marker and cell pools stably expressing human HER-2 were selected using methods known to those skilled in the art.

HER-2 expression was confirmed by flow cytometry. Briefly, following trypzinization, $10^6$ cells were centrifuged in FACS tubes; obtained pellets were resuspended in PBS (phosphate-buffered saline) supplemented with 2% of FCS. Cells were then incubated with the anti-HER-2 antibody trastuzumab (30 min, 4° C.), followed by centrifugation and washing (3 mL of PBS with 2% FCS). Cells were then resuspended as previously and incubated with anti-human IgG antibody (Fc gamma-specific) PE (Ebioscience) in the dark (30 min, 4° C.), prior to washing (4 mL PBS with 2% FCS). Flow cytometry was then performed on a FACS Calibur (BD).

HER-2-transfected EMT-6 cells were single cell-sorted by flow cytometry using a FACS ARIA II to isolate single cell clones. These were expanded and HER-2 expression was verified by flow cytometry.

Figure 9:
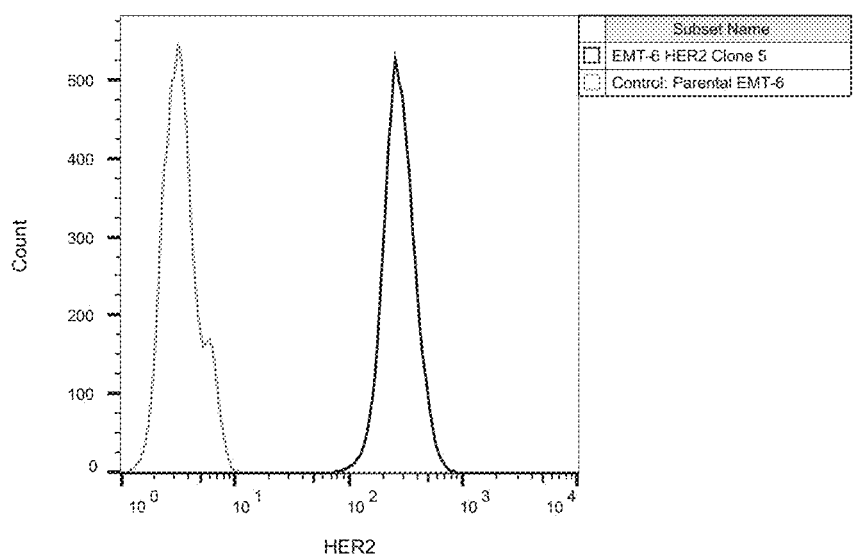

FIG. 9 shows the FACS analysis data of the clone selected for in vivo studies (Example 6).

Example 6

In Vivo Efficacy of Sortase A-Conjugated Trastuzumab-PNU-EDA-Gly$_5$ ADC in an Orthotopic Breast Cancer Model The in vivo efficacy of Trastuzumab-PNU-EDA-Gly$_5$ was evaluated in an immunocompetent orthotopic mouse model of HER-2-positive breast cancer. For this, $10^6$ EMT6 mouse breast cancer cells expressing human HER-2 (Example 6), previously determined to be suitable for in vivo growth, were implanted into the right mammary fat pads of female Balb/c mice. In addition, control animals were implanted with HER-2-negative EMT6 cells. In the following, primary tumor volumes were measured by calipering. After 13 days, when a mean tumor volume of 100-150 mm$^3$ was reached, tumor-bearing animals were randomized into groups of 6 animals each according to tumor sizes. Animals were treated on the same day (day 13, i.e. day of randomization) and 7 days later (day 20) by intravenous injection of the reference ADC Kadcyla® (15 mg/kg), Trastuzumab-PNU-EDA-Gly$_5$ (1 mg/kg) or vehicle control. Tumor sizes were monitored by calipering and animals whose tumor volume reached 1000-1500 mm$^3$ were terminated (FIGS. 10A-10D).

Figure 10:
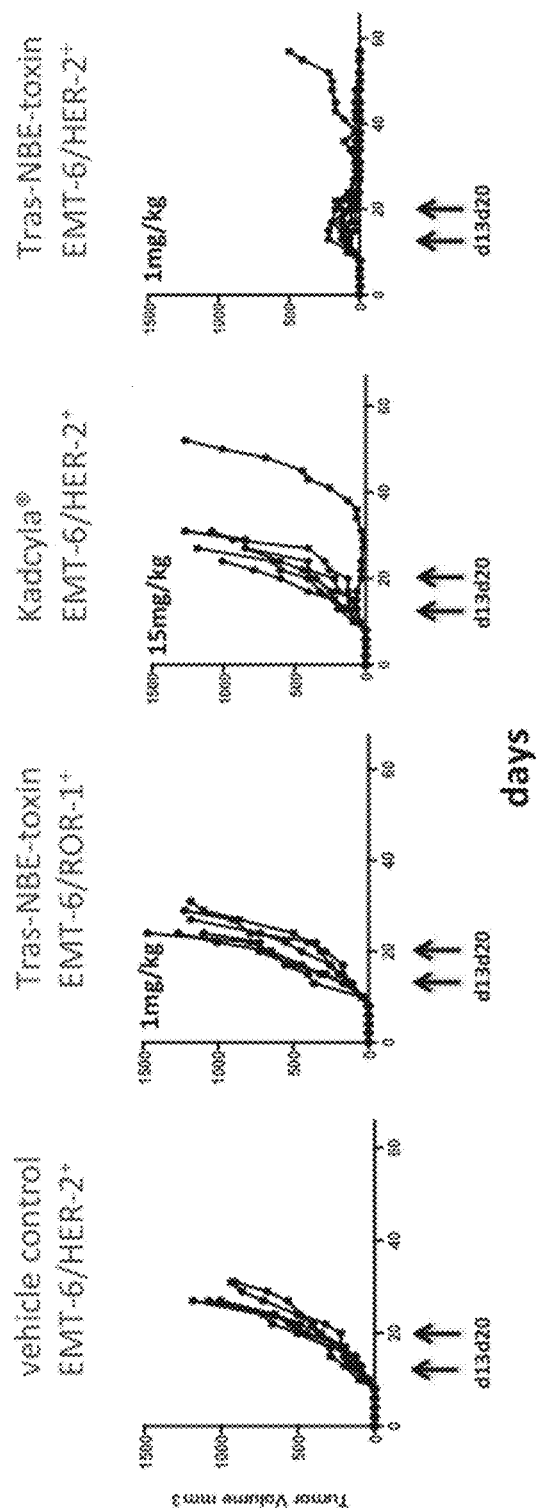

Tumors in vehicle control mice grew rapidly and reached an average size of approximately 1000 mm$^3$ within 30 days after transplantation of cells (FIG. 10A). Treatment with Kadcyla® had little effect on tumor growth in most animals. Only one out of six animals displayed a significant delay in tumor growth (FIG. 10C). In striking contrast, in all animals treated with Trastuzumab-PNU-EDA-Gly$_5$, the tumors continuously regressed during treatment and were essentially undetectable by day 30 after transplantation of the cells (FIG. 10D). No tumor was detectable most animals until day 60, and tumor recurrence was observed in only one animal around day 40. Significantly, the anti-tumor activity of Trastuzumab-PNU-EDA-Gly$_5$ was highly specific and treatment of mice bearing HER-2-negative tumors did not lead to tumor regression (FIG. 10B). Taken together, the data demonstrate that sortase-mediated site-specifically conjugated of Trastuzumab-EDA-Gly$_5$-PNU ADCs yielded an ADC with in vivo tumor cell killing activity far superior to the benchmark ADC Kadcyla®.

FIGURE LEGENDS

FIG. 1: Schematic drawing of site-specific sortase mediated antibody conjugation (SMAC-technology). The monoclonal antibodies need to be produced with C-terminal LPXTG sortase tags. The toxic payload needs to be produced to contain an oligoglycine peptide stretch (Gly$_n$-stretch) with a certain number of glycine residues in a row (n≥1 and ≤21, preferably m≥3 and ≤10, preferably n=3 or n=5, most preferably n=5). Sortase A enzyme from *Staphylococcus aureus* specifically recognizes the LPXTG pentapeptide motif and catalyzes the transpeptidation of the oligo-glycine peptide stretch to the threonine-glycine peptide bond of LPXTG, thereby generating a new stabile peptide bond between the threonine and the N-terminal glycine of the oligo-glycine stretch.

Figure 2:
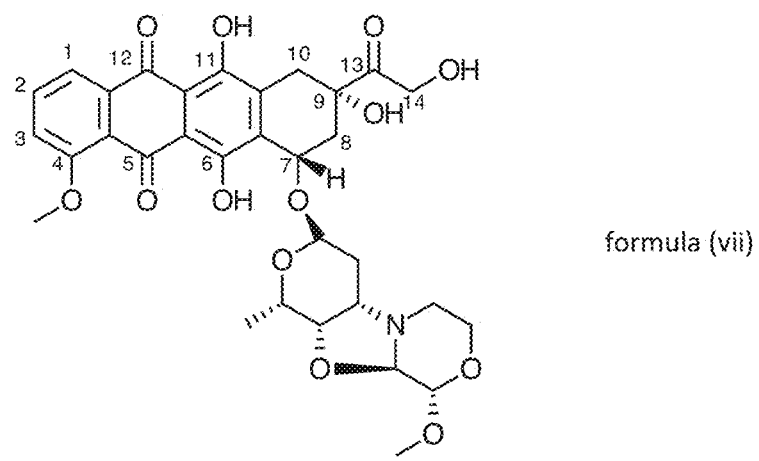

FIG. 2: Structure of PNU-159682 as described in the prior art (e.g. WO2009099741, or Quintieri et al (2005)), including the official anthracycline numbering system for reactive carbons of the tetracyclic aglycone structure.

FIGS. 3A-3B: (FIG. 3A) Structure of PNU derivative-EDA-Gly$_5$, called "PNU-EDA-Gly$_5$" herein, as utilized for the SMAC-technology conjugation to C-terminally LPETG sortase tagged monoclonal antibodies using sortase enzyme as disclosed in the Examples herein. (FIG. 3B) Synthesis scheme of anthracycline derivative PNU-EDA-Gly$_5$.

FIGS. 4A-4B: Dose response of the cytotoxic effects of the indicated ADCs on human Non-Hodgkin lymphoma cell line Karpas-299, expressing high levels of CD30 target on the cell surface (FIG. 4A), and on human Hodgkin lymphoma cell line L428 cells expressing very low levels of CD30 target in the cell surface (FIG. 4B). Adcetris refers to commercially available anti-CD30 ADC brentuximab-vedotin. Kadcyla refers to commercially available anti-HER-2/neu ADC T-DM1 (trastuzumab-emtansine). Both cell lines are negative for HER-2/neu, and therefore Kadcyla acts as a negative control ADC, that should not effect cell killing in a target-specific way. Cells were incubated with serial dilutions of ADCs for 4 days, after which CellTiter-Glo® Luminescent Solution (Promega) was added and viable cells were quantified by measuring the luminescence on a Tecan Infinity F200.

FIGS. 5A-5B: Dose response of the cytotoxic effects of the indicated ADCs on human breast cancer cell line SKBR3, expressing high levels of HER-2/neu (FIG. 5A) and human breast cancer cell line T47D expressing low levels of HER-2/neu (FIG. 5B). Cells were incubated with serial dilutions of ADCs for 4 days, after which CellTiter-Glo® Luminescent Solution (Promega) was added and viable cells were quantified by measuring the luminescence on a Tecan Infinity F200.

FIGS. 6A-6B: Additional PNU-159682 related anthracycline derivatives useful for site-specific-conjugation to LPXTG-tagged binding proteins or antibodies by SMAC-technology to produce BPDCs or ADCs. Only the preferred versions with Gly5-stretch are depicted. FIG. 6A depicts a derivative, in which the Gly5 amino acid stretch is directly coupled via its carboxy terminus to the A-Ring of the tetracyclic aglycone structure of the PNU derivative. FIG. 6B depicts a derivative in which a preferred ethylene-amino linker and Gly5 amino acid stretch is directly coupled to the A-Ring of the tetracyclic aglycone structure of the PNU derivative.

FIGS. 7A-7B: (FIG. 7A) Measurement of in vitro concentration of brentuximab-PNU-EDA-Gly$_5$ ADC (labeled as "cAc10-PNU ADC") and total IgG in mouse (A), rat (B), human (C) serum over 14 days. (FIG. 7B) Measurement of in vitro concentration of trastuzumab-emtansine (Kadcyla®) ADC and total IgG in mouse (A), rat (B) and human (C) serum over 14 days.

FIG. 8: In vivo plasma concentrations of ADC and total IgG measured at 6 time-points over a 21-day period following administration of Ac10-Gly5-PNU ADC in mice.

FIG. 9: Data of FACS analysis of EMT-6 HER-2 clone selected for in vivo studies following incubation with anti-HER-2 antibody trastuzumab and then incubation with fluorophore-containing anti-human IgG antibody (Fc gamma-specific) PE.

FIGS. 10A-D: In vivo evaluation of HER-2-specific ADCs in an immunocompetent orthotopic mouse model of HER2-positive breast cancer. EMT6 mouse breast cancer cells expressing human HER-2 (FIGS. 10A, 10C, 10D) or irrelevant antigen ROR-1 were grown in the mammary fat pads of Balb/c mice. On days 13 and 20, animals were treated i.v. with vehicle control (FIG. 10A), 1 mg/kg Trastuzumab-PNU159682 (FIG. 10B, 10D), or 15 mg/kg Kadcyla (FIG. 10C). Tumor growth was monitored until animals had to be sacrificed due to ethical reasons.

FIGS. 11A-B: Amino acid compositions of the C-terminally SMAC-technology™ conjugated IgH and IgL chains of the trastuzumab (FIG. 11A) and brentuximab (FIG. 11B) PNU-toxin derivative containing ADCs used for the studies, comprising the PNU derivative depicted in FIG. 3B linked through the amino group of the Gly5-stretch to the 4$^{th}$ amino acid of the sortase tag (highlighted in boldface print) via a peptide bond following sortase enzyme conjugation.

REFERENCES

Beerli et al. (2015) PloS One 10, e0131177
Dorr et al. (2014) PNAS 111, 13343-8
Quintieri L et al (2005), Clin Cancer Res. 2005 Feb. 15; 11(4):1608-17.
Roguska et al. (1994) PNAS 91, pp969-971
Perez et al. (2014) Drug Discovery Today 19, pp.869-881
Alley et al. (2008) Bioconjug. Chem. 19, pp. 759-765
Panowski et al. (2014) mAbs 6, pp. 34-45
Wolff A C et al (2013), J Clin Oncol. 2013 Nov. 1; 31(31): 3997-4013
Young K H (2014) Clinical Advances in Hematology & Oncology, Volume 12, Issue 4, Supplement 10
Spirig et al. (2011) Mol. Microbiol. 82, 1044-1059
Ducry & Stump (2010) Bioconjug. Chem. 21, 5-13,
McCombs et al. (2015) The AAPS Journal 17, 339-351
Mullard (2013) Nature Rev Drug Disc 12, 329-332
Doktor et al. (2014) Mol Cancer Ther 13, 2618-2629
Hartley & Hochhauser (2012) Curr. Opin. Pharmacol. 12, 398-402
Minotti (2004) Pharmacol. Rev 56, 185-229
Cancer and Chemotherpay—Antineoplastic Agents Vol. III, Stanley T. Crooke and Archie W. Prestayko (eds.), Academic Press 1981).

What is claimed is:

1. A method of producing a binding protein-drug conjugate (BPDC) comprising an anthracycline (PNU) derivative, the BPDC having the following formula:

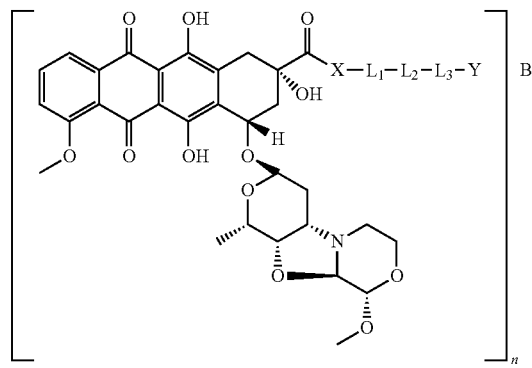

formula (iii)

or

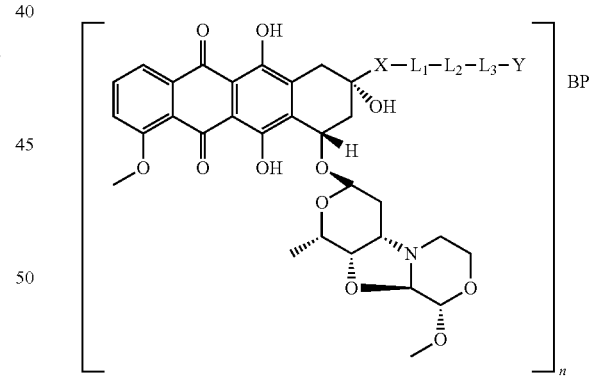

formula (iv)

wherein:
a) each of $L_1$-L3 represents a linker, wherein $L_1$ is optional and both $L_2$ and $L_3$ are mandatory,
b) $L_1$, when present, represents an alkylene-amino linker or an alkylene-diamino linker,
c) $L_2$ represents an oligo-glycine peptide ($Gly_p$), wherein p is an integer $\geq 1$ and $\leq 21$,
d) $L_3$ represents the amino acid residues 1-4 of a processed sortase tag pentapeptide motif,
e) X and Y each represent one or more optional linkers,
f) BP represents a binding protein selected from the group consisting of an antibody, a modified antibody format, an antigen-binding antibody derivative or fragment, and an antibody-based binding protein, and g) n is an integer ≥1 and ≤10, the method comprising conjugating, by means of a sortase enzyme, a binding protein carrying a sortase enzyme recognition motif, to at least one anthracycline (PNU) derivative conjugate comprising a derivative of the anthracycline PNU-159682 having the following formula (i) or formula (ii)

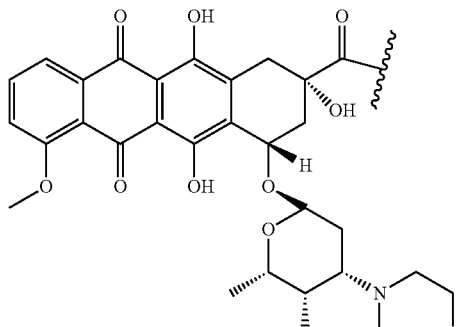

formula (i)

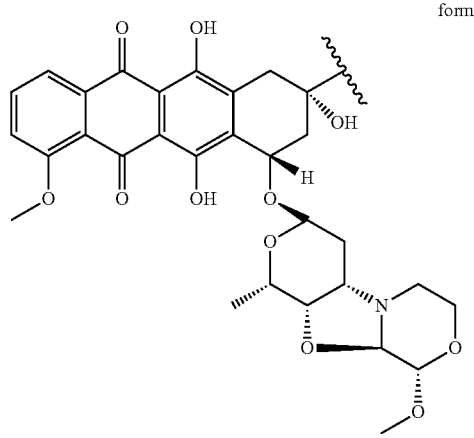

formula (ii)

to form the BPDC, said anthracycline (PNU) derivative conjugate comprising at its wavy line a linker structure $X-L_1-L_2$.

2. The method of claim 1, wherein Y, when present, is (N-terminal to C-terminal) Gly-Gly-Gly-Gly-Ser ($G_4S$) (SEQ ID NO: 8).

3. The method according to claim 1, wherein the oligo-glycine peptide is conjugated to the anthracycline (PNU) derivative by means of an ethylenediamino (EDA) linker, designated as $L_1$, which ethylenediamino linker is conjugated to the anthracycline (PNU) derivative by means of a first amide bond, and it is conjugated to the carboxy terminus of the oligo-glycine peptide by means of a second amide bond.

4. The method according to claim 1, wherein said sortase enzyme recognition motif comprises a pentapeptide.

5. The method according to claim 4, wherein said sortase enzyme recognition motif comprises at least one amino acid sequence selected from the group consisting of (N-terminal to C-terminal) NPQTN (SEQ ID NO: 9), LPXTG (SEQ ID NO: 5), LPXSG (SEQ ID NO: 6), and LAXTG (SEQ ID NO: 7), wherein X in each of SEQ ID NOs: 5-7 represents any amino acid.

6. The method according to claim 1, wherein the anthracycline (PNU) derivative is conjugated, by means of the two or more linkers, to the carboxy terminus of the binding protein, or to the carboxy terminus of at least one domain or subunit thereof.

7. The method according to claim 1, wherein the binding protein binds at least one entity selected from the group consisting of a receptor, an antigen, a growth factor, a cytokine, and a hormone.

8. The method according to claim 1, wherein the binding protein is an antibody.

9. The method according to claim 1, wherein the binding protein is an antibody that binds HER-2.

10. The method according to claim 1, wherein the binding protein is an antibody that binds CD30.

11. The method according to claim 1, wherein the BPDC has the following formula:

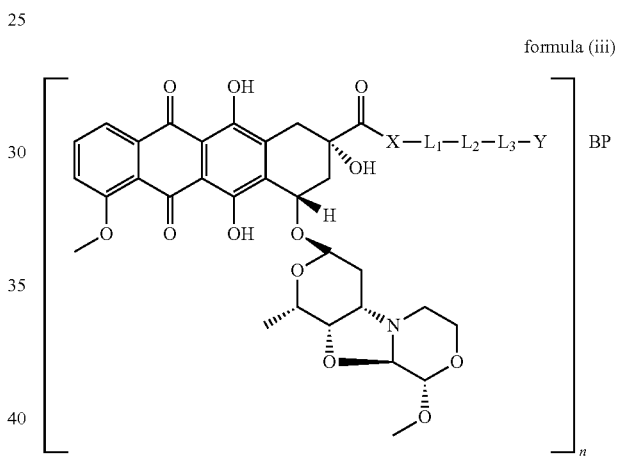

formula (iii)

wherein a) X is absent,
b) $L_1$ represents ethylenediamine (EDA),
c) $L_2$ represents an oligo-glycine peptide ($Gly_p$), wherein p is an integer ≥1 and ≤21,
d) $L_3$ consists of amino acid residues 1-4 of a processed sortase enzyme recognition motif (N-terminal to C-terminal) Leu-Pro-Xaa-Thr-Gly (LPXTG) (SEQ ID NO: 5, wherein Xaa is any amino acid),
e) Y, when present, is (N-terminal to C-terminal) Gly-Gly-Gly-Gly-Ser ($G_4S$) (SEQ ID NO: 8),
f) BP is an IgG antibody, and
g) n is an integer ≥1 and ≤10.

12. The method according to claim 11, wherein the N-terminal Gly of Y is linked to the last C-terminal Cys amino acid of at least one light chain of the antibody.

13. The method according to claim 11, wherein the N-terminal Gly of Y is linked to the last C-terminal Ser amino acid of at least one light chain of the antibody.

* * * * *

SEQUENCE LISTING

<160> NUMBER OF SEQ ID NOS: 13

<210> SEQ ID NO 1
<211> LENGTH: 459
<212> TYPE: PRT
<213> ORGANISM: Artificial

-continued

<220> FEATURE:
<223> OTHER INFORMATION: Trastuzumab-HC-LPETGGGGG-PNU-toxin

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

```
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
        435                 440                 445
Gly Lys Leu Pro Glu Thr Gly Gly Gly Gly Gly
    450                 455

<210> SEQ ID NO 2
<211> LENGTH: 228
<212> TYPE: PRT
<213> ORGANISM: artificial
<220> FEATURE:
<223> OTHER INFORMATION: Trastuzumab-LC-GGGGS-LPETGGGGG-PNU-toxin

<400> SEQUENCE: 2

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Asp Val Asn Thr Ala
            20                  25                  30
Val Ala Trp Tyr Gln Gln Lys Pro Gly Lys Ala Pro Lys Leu Leu Ile
        35                  40                  45
Tyr Ser Ala Ser Phe Leu Tyr Ser Gly Val Pro Ser Arg Phe Ser Gly
    50                  55                  60
Ser Arg Ser Gly Thr Asp Phe Thr Leu Thr Ile Ser Ser Leu Gln Pro
65                  70                  75                  80
Glu Asp Phe Ala Thr Tyr Tyr Cys Gln Gln His Tyr Thr Thr Pro Pro
                85                  90                  95
Thr Phe Gly Gln Gly Thr Lys Val Glu Ile Lys Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys Gly Gly Gly Ser Leu Pro Glu Thr Gly
    210                 215                 220
Gly Gly Gly Gly
225

<210> SEQ ID NO 3
<211> LENGTH: 456
<212> TYPE: PRT
<213> ORGANISM: artificial
<220> FEATURE:
<223> OTHER INFORMATION: Brentuximab-HC-LPETGGGGG-PNU-toxin

<400> SEQUENCE: 3

Gln Ile Gln Leu Gln Gln Ser Gly Pro Glu Val Val Lys Pro Gly Ala
```

-continued

```
1               5                   10                  15
Ser Val Lys Ile Ser Cys Lys Ala Ser Gly Tyr Thr Phe Thr Asp Tyr
                20                  25                  30

Tyr Ile Thr Trp Val Lys Gln Lys Pro Gly Gln Gly Leu Glu Trp Ile
                35                  40                  45

Gly Trp Ile Tyr Pro Gly Ser Gly Asn Thr Lys Tyr Asn Glu Lys Phe
                50                  55                  60

Lys Gly Lys Ala Thr Leu Thr Val Asp Thr Ser Ser Ser Thr Ala Phe
65                  70                  75                  80

Met Gln Leu Ser Ser Leu Thr Ser Glu Asp Thr Ala Val Tyr Phe Cys
                85                  90                  95

Ala Asn Tyr Gly Asn Tyr Trp Phe Ala Tyr Trp Gly Gln Gly Thr Gln
                100                 105                 110

Val Thr Val Ser Ala Ala Ser Thr Lys Gly Pro Ser Val Phe Pro Leu
                115                 120                 125

Ala Pro Ser Ser Lys Ser Thr Ser Gly Gly Thr Ala Ala Leu Gly Cys
                130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
                180                 185                 190

Leu Gly Thr Gln Thr Tyr Ile Cys Asn Val Asn His Lys Pro Ser Asn
                195                 200                 205

Thr Lys Val Asp Lys Lys Val Glu Pro Lys Ser Cys Asp Lys Thr His
                210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
                260                 265                 270

Val Lys Phe Asn Trp Tyr Val Asp Gly Val Glu Val His Asn Ala Lys
                275                 280                 285

Thr Lys Pro Arg Glu Glu Gln Tyr Asn Ser Thr Tyr Arg Val Val Ser
                290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Arg Asp Glu Leu Thr Lys Asn Gln Val Ser Leu Thr Cys Leu
                355                 360                 365

Val Lys Gly Phe Tyr Pro Ser Asp Ile Ala Val Glu Trp Glu Ser Asn
                370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430
```

-continued

His Asn His Tyr Thr Gln Lys Ser Leu Ser Leu Ser Pro Gly Lys Leu
435 440 445

Pro Glu Thr Gly Gly Gly Gly Gly
450 455

<210> SEQ ID NO 4
<211> LENGTH: 232
<212> TYPE: PRT
<213> ORGANISM: artificial
<220> FEATURE:
<223> OTHER INFORMATION: Brentuximab-LC-GGGGS-LPETGGGGG-PNU-toxin

<400> SEQUENCE: 4

Asp Ile Val Leu Thr Gln Ser Pro Ala Ser Leu Ala Val Ser Leu Gly
1 5 10 15

Gln Arg Ala Thr Ile Ser Cys Lys Ala Ser Gln Ser Val Asp Phe Asp
20 25 30

Gly Asp Ser Tyr Met Asn Trp Tyr Gln Gln Lys Pro Gly Gln Pro Pro
35 40 45

Lys Val Leu Ile Tyr Ala Ala Ser Asn Leu Glu Ser Gly Ile Pro Ala
50 55 60

Arg Phe Ser Gly Ser Gly Ser Gly Thr Asp Phe Thr Leu Asn Ile His
65 70 75 80

Pro Val Glu Glu Glu Asp Ala Ala Thr Tyr Tyr Cys Gln Gln Ser Asn
85 90 95

Glu Asp Pro Trp Thr Phe Gly Gly Gly Thr Lys Leu Glu Ile Lys Arg
100 105 110

Thr Val Ala Ala Pro Ser Val Phe Ile Phe Pro Pro Ser Asp Glu Gln
115 120 125

Leu Lys Ser Gly Thr Ala Ser Val Val Cys Leu Leu Asn Asn Phe Tyr
130 135 140

Pro Arg Glu Ala Lys Val Gln Trp Lys Val Asp Asn Ala Leu Gln Ser
145 150 155 160

Gly Asn Ser Gln Glu Ser Val Thr Glu Gln Asp Ser Lys Asp Ser Thr
165 170 175

Tyr Ser Leu Ser Ser Thr Leu Thr Leu Ser Lys Ala Asp Tyr Glu Lys
180 185 190

His Lys Val Tyr Ala Cys Glu Val Thr His Gln Gly Leu Ser Ser Pro
195 200 205

Val Thr Lys Ser Phe Asn Arg Gly Glu Cys Gly Gly Gly Gly Ser Leu
210 215 220

Pro Glu Thr Gly Gly Gly Gly Gly
225 230

<210> SEQ ID NO 5
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (3)..(3)
<223> OTHER INFORMATION: Any amino acid

<400> SEQUENCE: 5

Leu Pro Xaa Thr Gly
1 5

```
<210> SEQ ID NO 6
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (3)..(3)
<223> OTHER INFORMATION: Any amino acid

<400> SEQUENCE: 6

Leu Pro Xaa Ser Gly
1               5

<210> SEQ ID NO 7
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (3)..(3)
<223> OTHER INFORMATION: Any amino acid

<400> SEQUENCE: 7

Leu Ala Xaa Thr Gly
1               5

<210> SEQ ID NO 8
<211> LENGTH: 5
<212> TYPE: PRT
<213> ORGANISM: Artificial sequence
<220> FEATURE:
<223> OTHER INFORMATION: Synthetic peptide

<400> SEQUENCE: 8

Gly Gly Gly Gly Ser
1               5

<210> SEQ ID NO 9
<211> LENGTH: 5
<212> TYPE: PRT
<213> ORGANISM: Artificial sequence
<220> FEATURE:
<223> OTHER INFORMATION: Synthetic peptide

<400> SEQUENCE: 9

Asn Pro Gln Thr Asn
1               5

<210> SEQ ID NO 10
<211> LENGTH: 5
<212> TYPE: PRT
<213> ORGANISM: Artificial sequence
<220> FEATURE:
<223> OTHER INFORMATION: Synthetic peptide

<400> SEQUENCE: 10

Leu Ala Glu Thr Gly
1               5
```

```
<210> SEQ ID NO 11
<211> LENGTH: 14
<212> TYPE: PRT
<213> ORGANISM: Artificial sequence
<220> FEATURE:
<223> OTHER INFORMATION: Synthetic peptide

<400> SEQUENCE: 11

Leu Pro Glu Thr Gly Gly Trp Ser His Pro Gln Phe Glu Lys
1               5                   10

<210> SEQ ID NO 12
<211> LENGTH: 19
<212> TYPE: PRT
<213> ORGANISM: Artificial sequence
<220> FEATURE:
<223> OTHER INFORMATION: Synthetic peptide

<400> SEQUENCE: 12

Gly Gly Gly Gly Ser Leu Pro Glu Thr Gly Gly Trp Ser His Pro Gln
1               5                   10                  15

Phe Glu Lys

<210> SEQ ID NO 13
<211> LENGTH: 5
<212> TYPE: PRT
<213> ORGANISM: Artificial sequence
<220> FEATURE:
<223> OTHER INFORMATION: Synthetic peptide

<400> SEQUENCE: 13

Leu Pro Glu Thr Gly
1               5
```